United States Patent
Suddaby

(10) Patent No.: US 10,314,718 B2
(45) Date of Patent: Jun. 11, 2019

(54) EXPANDABLE INTERVERTEBRAL FUSION IMPLANT

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 293 days.

(21) Appl. No.: 15/273,032

(22) Filed: Sep. 22, 2016

(65) Prior Publication Data
US 2018/0078384 A1 Mar. 22, 2018

(51) Int. Cl.
A61F 2/44 (2006.01)
A61F 2/30 (2006.01)
(Continued)

(52) U.S. Cl.
CPC ............ *A61F 2/4425* (2013.01); *A61F 2/446* (2013.01); *A61F 2/447* (2013.01); *A61F 2/4455* (2013.01); *A61F 2/4465* (2013.01); *A61F 2002/30224* (2013.01); *A61F 2002/30471* (2013.01); *A61F 2002/30537* (2013.01); *A61F 2002/30538* (2013.01); *A61F 2002/30555* (2013.01);
(Continued)

(58) Field of Classification Search
CPC ........ A61F 2/44; A61F 2/4425; A61F 2/4455; A61F 2/446; A61F 2/4465; A61F 2/447; A61F 2002/4475
USPC .......................................... 623/17.11–17.16
See application file for complete search history.

(56) References Cited

U.S. PATENT DOCUMENTS

| 5,505,732 | A | 4/1996 | Michelson |
| 5,653,762 | A | 8/1997 | Pisharodi |

(Continued)

FOREIGN PATENT DOCUMENTS

| WO | 2008/011371 | 1/2008 |
| WO | 2009/064787 | 5/2009 |
| WO | 2009/105182 | 8/2009 |

OTHER PUBLICATIONS

Sahara AL Expandable Stabilization System; Advertisement flyer; Available from K2M, Inc. Leesburg, Virginia; Published as early as Oct. 20, 2015.

(Continued)

*Primary Examiner* — Eric S Gibson
(74) *Attorney, Agent, or Firm* — Simpson & Simpson, PLLC

(57) ABSTRACT

An expandable intervertebral fusion implant including an inferior component, a superior component arranged to telescopingly engage the inferior component, and a port arranged in the inferior or superior component. When a first material is introduced through the port, the inferior and superior components are displaced vertically. Each of the inferior and/or superior components can include telescoping components which allow the inferior and/or superior components to be expanded along the length and/or width of the implant before the inferior and superior components are displaced vertically. The expandable intervertebral fusion implant can be expanded with, and locked in place, hydraulic and/or hardenable material. Alternatively, the expandable intervertebral fusion implant can be expanded using a mechanical implement and then hardenable material can be introduced into the implant to maintain the implant in the expanded position.

20 Claims, 31 Drawing Sheets

(51) Int. Cl.
*A61F 2/46* (2006.01)
*A61F 2/48* (2006.01)

(52) U.S. Cl.
CPC .............. *A61F 2002/30556* (2013.01); *A61F 2002/30579* (2013.01); *A61F 2002/30583* (2013.01); *A61F 2002/30593* (2013.01); *A61F 2002/30601* (2013.01); *A61F 2002/30622* (2013.01); *A61F 2002/30693* (2013.01); *A61F 2002/4475* (2013.01); *A61F 2002/4692* (2013.01); *A61F 2002/4693* (2013.01); *A61F 2002/484* (2013.01); *A61F 2002/485* (2013.01)

(56) References Cited

U.S. PATENT DOCUMENTS

| | | | |
|---|---|---|---|
| 5,665,122 A | 9/1997 | Kambin | |
| 5,683,463 A | 11/1997 | Godefroy et al. | |
| 5,827,328 A | 10/1998 | Buttermann | |
| 6,176,881 B1 | 1/2001 | Schär et al. | |
| 6,190,414 B1 * | 2/2001 | Young | A61F 2/447 606/247 |
| 6,395,034 B1 | 5/2002 | Suddaby | |
| 6,524,341 B2 | 2/2003 | Läng et al. | |
| 6,837,850 B2 | 1/2005 | Suddaby | |
| 6,958,077 B2 | 10/2005 | Suddaby | |
| 6,969,405 B2 * | 11/2005 | Suddaby | A61F 2/441 623/17.12 |
| 6,991,653 B2 | 1/2006 | White et al. | |
| 7,309,358 B2 | 12/2007 | Berry et al. | |
| 7,597,714 B2 | 10/2009 | Suddaby | |
| 7,615,078 B2 | 11/2009 | White et al. | |
| 7,628,800 B2 | 12/2009 | Sherman et al. | |
| 7,648,529 B2 | 1/2010 | An et al. | |
| 7,731,752 B2 * | 6/2010 | Edie | A61F 2/44 623/17.11 |
| 7,794,501 B2 * | 9/2010 | Edie | A61F 2/44 623/17.12 |
| 8,007,535 B2 | 8/2011 | Hudgins et al. | |
| 8,057,549 B2 | 11/2011 | Buttermann et al. | |
| 8,070,813 B2 * | 12/2011 | Grotz | A61F 2/4465 623/17.11 |
| 8,123,809 B2 * | 2/2012 | Melkent | A61F 2/44 623/17.11 |
| 8,187,328 B2 * | 5/2012 | Melkent | A61F 2/44 623/17.11 |
| 8,246,630 B2 | 8/2012 | Manzi et al. | |
| 8,273,126 B2 | 9/2012 | Lindner | |
| 8,303,663 B2 | 11/2012 | Jimenez et al. | |
| 8,394,143 B2 * | 3/2013 | Grotz | A61F 2/4465 623/17.11 |
| 8,425,611 B2 * | 4/2013 | Dewey | A61F 2/44 623/17.12 |
| 8,435,296 B2 * | 5/2013 | Kadaba | A61F 2/44 623/17.12 |
| 8,480,738 B2 | 7/2013 | Edie et al. | |
| 8,480,741 B2 | 7/2013 | Grotz et al. | |
| 8,512,406 B2 | 8/2013 | White et al. | |
| 8,568,481 B2 | 10/2013 | Olmos et al. | |
| 8,696,751 B2 | 4/2014 | Ashley et al. | |
| 8,900,312 B2 | 12/2014 | McLean et al. | |
| 8,932,302 B2 | 1/2015 | Jimenez et al. | |
| 8,932,355 B2 * | 1/2015 | Grotz | A61F 2/442 623/17.16 |
| 8,956,413 B2 | 2/2015 | Ashley et al. | |
| 8,992,620 B2 * | 3/2015 | Ashley | A61F 2/4455 623/17.16 |
| 9,011,499 B1 | 4/2015 | Kiester | |
| 9,028,550 B2 * | 5/2015 | Shulock | A61F 2/441 623/17.11 |
| 9,066,760 B2 | 6/2015 | Taber et al. | |
| 9,078,767 B1 | 7/2015 | McLean | |
| 9,084,686 B1 | 7/2015 | McLean et al. | |
| 2003/0191531 A1 | 10/2003 | Berry et al. | |
| 2004/0102774 A1 * | 5/2004 | Trieu | A61B 17/7097 606/86 A |
| 2005/0256576 A1 * | 11/2005 | Moskowitz | A61F 2/441 623/17.12 |
| 2007/0093901 A1 * | 4/2007 | Grotz | A61F 2/442 623/17.11 |
| 2007/0233254 A1 * | 10/2007 | Grotz | A61F 2/442 623/17.11 |
| 2007/0250172 A1 | 10/2007 | Moskowitz et al. | |
| 2007/0255413 A1 * | 11/2007 | Edie | A61F 2/44 623/17.16 |
| 2008/0058930 A1 * | 3/2008 | Edie | A61F 2/44 623/17.11 |
| 2008/0140207 A1 | 6/2008 | Olmos et al. | |
| 2008/0167726 A1 * | 7/2008 | Melkent | A61F 2/44 623/23.48 |
| 2008/0215153 A1 | 9/2008 | Butterman et al. | |
| 2009/0182343 A1 * | 7/2009 | Trudeau | A61F 2/4657 606/102 |
| 2009/0216331 A1 * | 8/2009 | Grotz | A61F 2/442 623/17.16 |
| 2009/0270987 A1 * | 10/2009 | Heinz | A61F 2/44 623/17.16 |
| 2010/0004752 A1 | 1/2010 | White et al. | |
| 2010/0057204 A1 * | 3/2010 | Kadaba | A61F 2/442 623/17.12 |
| 2010/0076559 A1 | 3/2010 | Bagga et al. | |
| 2010/0114318 A1 * | 5/2010 | Gittings | A61F 2/442 623/17.12 |
| 2010/0198352 A1 | 8/2010 | Edie et al. | |
| 2010/0204794 A1 * | 8/2010 | Jarzem | A61B 17/8805 623/17.12 |
| 2010/0286783 A1 * | 11/2010 | Lechmann | A61F 2/3094 623/17.12 |
| 2011/0130835 A1 * | 6/2011 | Ashley | A61F 2/44 623/17.11 |
| 2011/0270398 A1 * | 11/2011 | Grotz | A61F 2/442 623/17.12 |
| 2011/0319996 A1 * | 12/2011 | Barrall | A61F 2/442 623/17.12 |
| 2012/0059479 A1 | 3/2012 | Buttermann et al. | |
| 2012/0101576 A1 * | 4/2012 | Dewey | A61F 2/44 623/17.11 |
| 2012/0116518 A1 * | 5/2012 | Grotz | A61F 2/442 623/17.16 |
| 2012/0271419 A1 * | 10/2012 | Marik | A61F 2/4425 623/17.12 |
| 2013/0131808 A1 * | 5/2013 | Suh | A61F 2/30721 623/17.16 |
| 2013/0190875 A1 * | 7/2013 | Shulock | A61F 2/441 623/17.12 |
| 2013/0231747 A1 | 9/2013 | Olmos et al. | |
| 2013/0253650 A1 * | 9/2013 | Ashley | A61F 2/4455 623/17.16 |
| 2013/0261748 A1 | 10/2013 | Ashley et al. | |
| 2014/0012383 A1 | 1/2014 | Triplett et al. | |
| 2014/0207236 A1 | 7/2014 | Prevost et al. | |
| 2014/0277476 A1 | 9/2014 | McLean et al. | |
| 2014/0277480 A1 | 9/2014 | Prevost et al. | |
| 2015/0012098 A1 * | 1/2015 | Eastlack | A61F 2/447 623/17.15 |
| 2015/0081022 A1 | 3/2015 | McLean et al. | |
| 2015/0148907 A1 | 5/2015 | Kleiner et al. | |
| 2015/0289988 A1 * | 10/2015 | Ashley | A61F 2/4455 623/17.15 |
| 2018/0078384 A1 * | 3/2018 | Suddaby | A61F 2/4425 |

OTHER PUBLICATIONS

Stryker; Stryker AccuLIF® Expandable Lumbar Interbody Fusion Technology; 2014; Product Summary Sheet available from http://www.stryker.com/en-us/products/Spine/

(56) References Cited

OTHER PUBLICATIONS

InterbodyVertebralBodyReplacement/AccuLIFExpandableLumbarInterbodyFusionTechnology/index.htm.

* cited by examiner

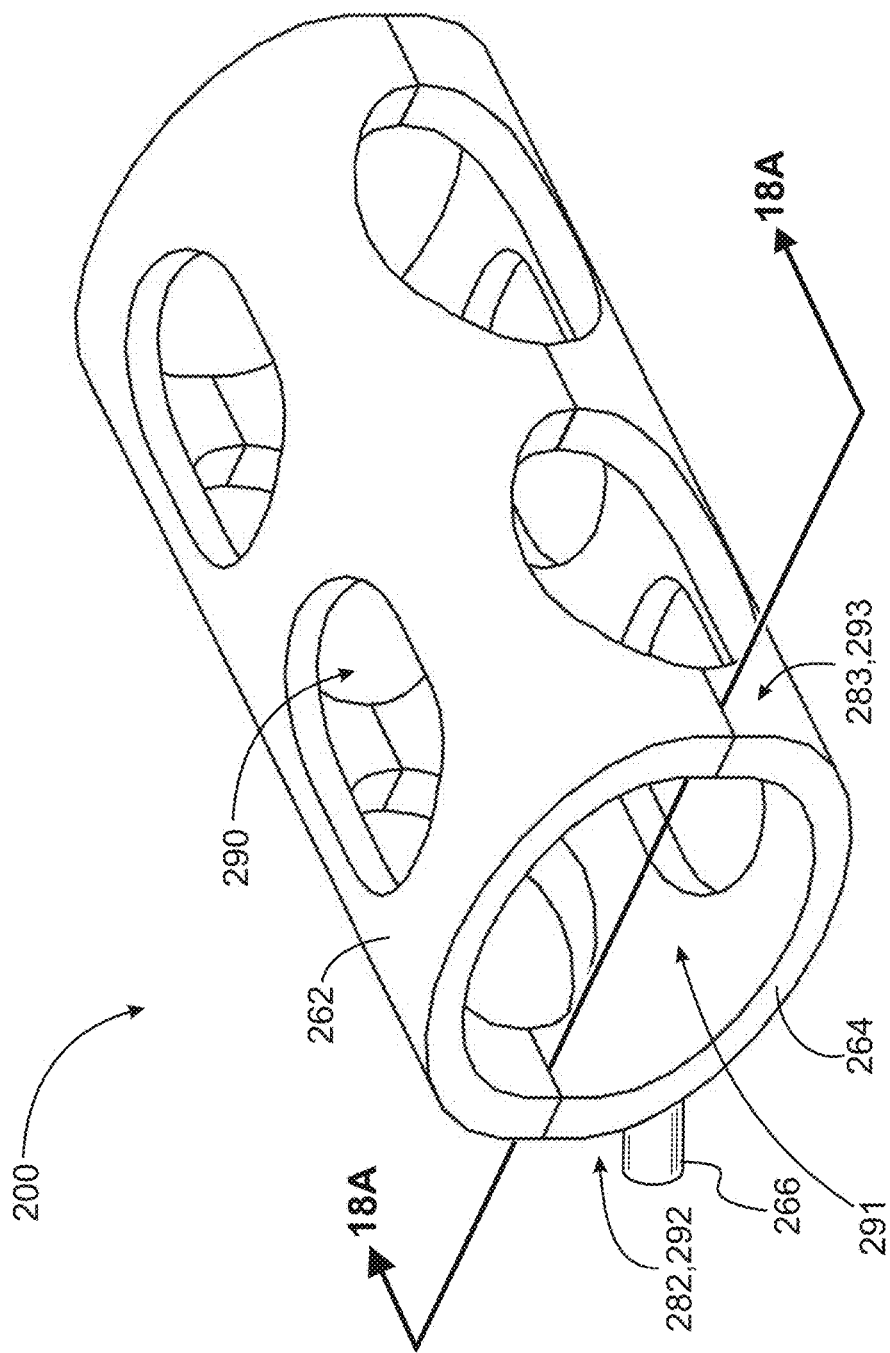

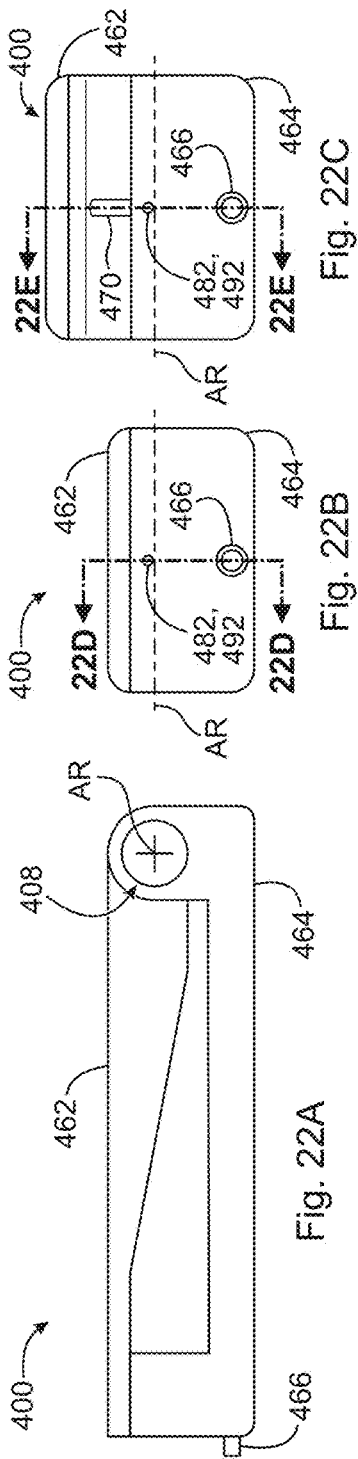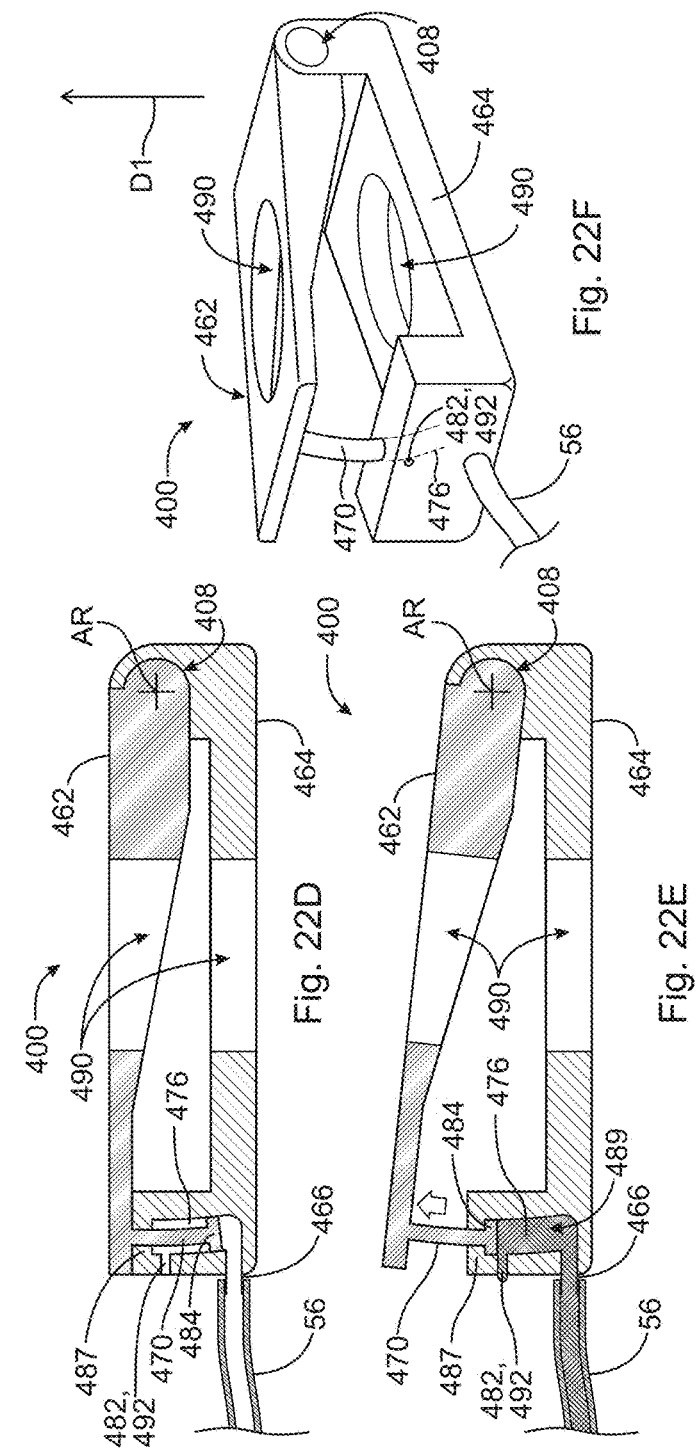

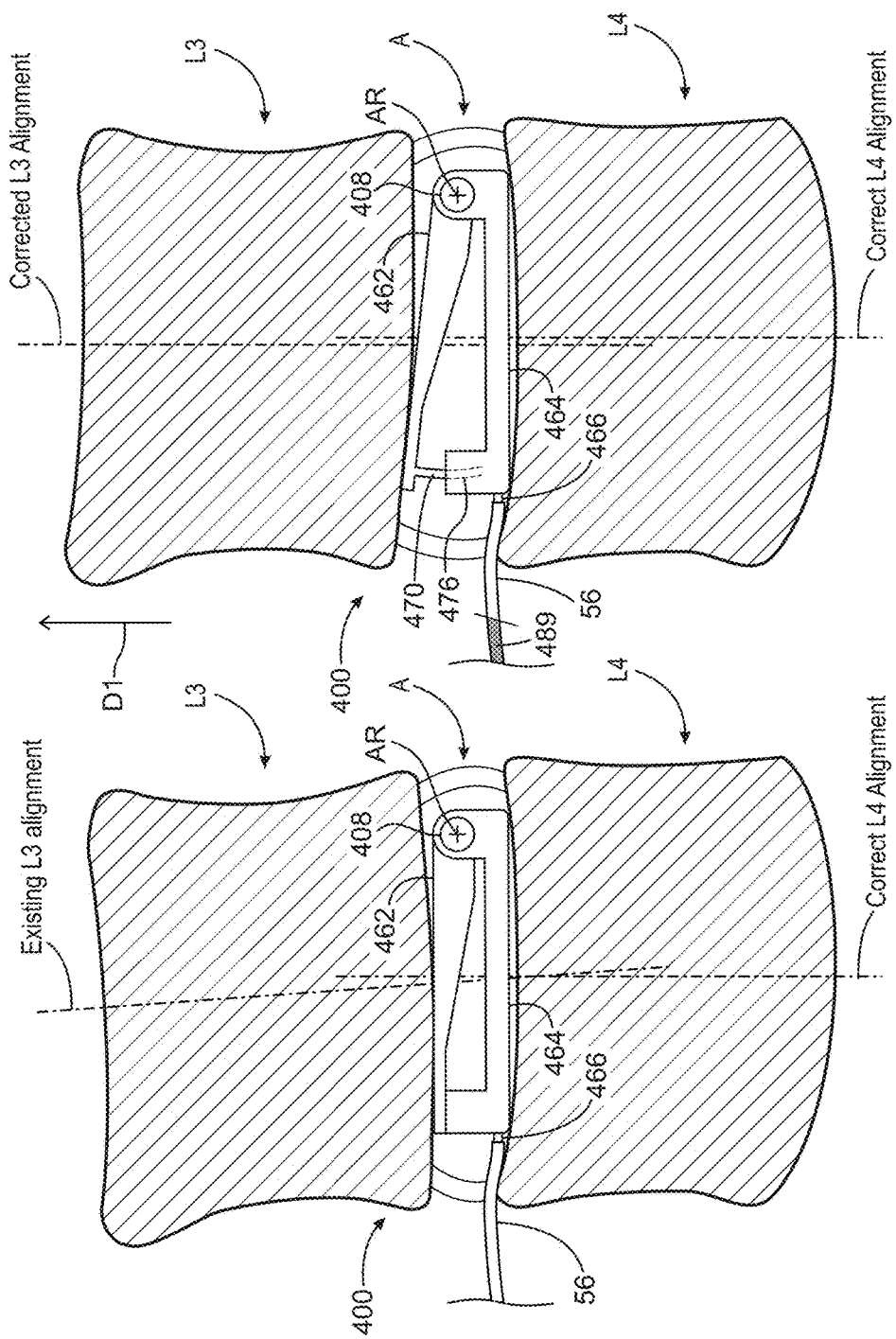

EXPANDABLE INTERVERTEBRAL FUSION IMPLANT

FIELD

The invention relates to spinal surgery, more particularly to intervertebral prosthesis, and, even more specifically, to an expandable intervertebral fusion implant.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae (C1-C7) form the neck, support the head and neck, and allow nodding and shaking of the head. The thoracic vertebrae (T1-T12) join with the ribs to form the rib cage. The five lumbar vertebrae (L1-L5) carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal, or neuro canal. The spinal cord and spinal nerves pass through the spinal canal, which protects them from injury. The spinal cord is the major column of nerve tissue that is connected to the brain and serves as an information superhighway between the brain and the body. The nerves in the spinal cord branch off to form pairs of nerve roots that travel through the small openings between the vertebrae and the intervertebral foramens.

The repetitive forces which act on these intervertebral discs during repetitive day-to-day activities of bending, lifting and twisting cause them to break down or degenerate over time. Overt trauma, or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and even chemical irritation of surrounding neural elements cause pain, attended by varying degrees of disability. In addition, loss of disc space height relaxes tension on the longitudinal ligaments, thereby contributing to varying degrees of spinal instability such as spinal curvature.

Neural irritation and instability resulting from severe disc damage has been treated by removing the damaged disc and fusing adjacent vertebral elements. Removal of the disc relieves the mechanical and chemical irritation of neural elements, while osseous union solves the problem of instability. For example, in one surgical procedure, known as a discectomy (or diskectomy), the surgeon removes the nucleus of the disk and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 and SP4, transverse processes TP3A and TP44A, and intervertebral foramen IF. FIG. 4 is a top view of the section of the spinal column shown in FIG. 3, with the L3 vertebra removed to expose annulus A and nucleus N of disc $D_{L3-L4}$. FIG. 5 is an anterior perspective view of the section of the spinal column shown in FIG. 4. FIG. 6 is a partial cross-sectional view of the section of the spinal column shown in FIG. 5, but with vertebra L3 in place atop disc $D_{L3-L4}$.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union.

Intervertebral prosthesis in various forms have therefore been used to provide immediate stability and to protect and preserve an environment that fosters growth of grafted bone such that a structurally significant bony fusion can occur.

U.S. Pat. No. 5,505,732 (Michelson) describes an apparatus and a method of inserting spinal implants in which an intervertebral space is first distracted, a hollow sleeve having teeth at one end is then driven into the vertebrae adjacent that disc space. A drill is then passed through the hollow sleeve removing disc and bone in preparation for receiving the spinal implant which is then inserted through the sleeve. Unfortunately, the apparatus does not enable a doctor to achieve great ranges of implant height, or to adjust taper angle for kyphotic or lordotic conditions.

U.S. Pat. No. 5,665,122 (Kambin) describes an expandable intervertebral cage and surgical method including a pair of cage components, each generally in the shape of a half cylinder. Each of the cage components provides a corresponding abutting conically shaped recess that cooperates with a conical end portion of an expansion screw. One of the cage components carries a fitting with an internally threaded bore that receives external threads of the expansion screw. As the expansion screw advances into the cage, the conically shaped end portion of the expansion screw engages the conically shaped recesses on the cage components to expand the two cage components apart until they are in contact with the vertebral plates of adjacent vertebrae. Like the apparatus described in the Michelson patent, the expandable intervertebral cage described in the Kambin patent does not enable a doctor to achieve great ranges of implant height. Nor does the expandable cage enable a doctor to achieve ranges of implant length or implant width.

Typical intervertebral implants have limited applicability due to the marked variation in disc space shape and height that results from biologic variation or pathologic change. For example, if a disc space is 20 mm in height, a circular implant bridging this gap requires a minimum diameter of 20 mm just to contact the end plate of the vertebral bone. Generally, endplate disruption must occur to allow a generous bony union, meaning an additional 2-3 mm must be added to either end, resulting in a final implant size of 24-26 mm. During implantation from an anterior approach, excessive retraction of the great blood vessels is required, which greatly enhances the risk of devastating complications such as vascular tears or thrombosis. On the other hand during a posterior approach, large implant diameters may require excessive traction on neural elements for adequate placement, even if all posterior bony elements are removed. In some instances an adequate implant size cannot be inserted posteriorly, particularly if there is a significant degree of ligamentous laxity requiring higher degrees of distraction to obtain stability by tautening the annular ligamentous tension band.

Compromising on implant size risks sub-optimal stability or a loose implant which has a greater chance for migration within or expulsion from the disc space. The alternative of excessively retracting neural elements to facilitate a posterior implant application results in neuropraxia at best and permanent neural damage at worst.

Thus, there is a long-felt need for an expandable intervertebral fusion implant which can be inserted into a distracted disc space in an unexpanded state and then expanded to a desired length, and/or depth, and/or height such that minimally invasive techniques can be employed and stable long term fusion of adjacent vertebral elements is achieved.

SUMMARY

According to aspects illustrated herein, there is provided an expandable intervertebral fusion implant including an inferior component, a superior component telescopingly engageable with the inferior component, and a port arranged in the inferior or the superior component. When a first material is introduced through the port and into the inferior or the superior component, the inferior component is displaced in a first direction relative to the superior component.

According to aspects illustrated herein, there is provided an expandable intervertebral fusion implant having a proximal end and a distal end, the expandable intervertebral fusion implant including an inferior component, a superior component arranged to telescopingly engage the inferior component, and an input port and an output port within the proximal end and within the inferior or superior component. When the superior component is expanded to a first position relative to the inferior component, a first material is introduced into and through the hollow channel to maintain the position of the superior and inferior components.

According to aspects illustrated herein, there is provided a method of expanding an intervertebral fusion implant in a disc space between vertebral bodies including inserting the intervertebral fusion implant in an unexpanded state within the disc space, the intervertebral fusion implant having a superior component, an inferior component, a port, and a cavity formed between the superior and inferior components, and introducing a first material through the port and into the inferior component or the superior component of the intervertebral fusion implant such that a distance between the superior and inferior component increases in a first direction and the cavity increases in size.

According to aspects illustrated herein, there is provided a method of expanding an intervertebral fusion implant in a disc space between vertebral bodies including inserting the intervertebral fusion implant in an unexpanded state within the disc space, the intervertebral fusion implant having a superior component, an inferior component, a port, and a cavity formed between the superior and inferior components, expanding the intervertebral fusion implant in a first direction such that a distance between the superior and inferior component increases in a first direction and the cavity increases in size, and introducing a first material through the port and into the inferior component or the superior component of the intervertebral fusion implant such that the distance between the superior and inferior components is maintained.

A primary object is to provide an expandable intervertebral fusion implant which can be inserted into a distracted disc space in an unexpanded state and then expanded to a desired length, and/or width, and/or height such that minimally invasive techniques can be employed and stable long term fusion of adjacent vertebral elements is achieved.

A further object is to provide an expandable intervertebral fusion implant including telescopingly engaged members which can be filled with hardenable material to cause a desired expansion.

Still another object is to provide an expandable intervertebral fusion implant including telescopingly engaged members which can be expanded initially to a desired state and thereafter filled with hardenable material to maintain the desired expanded state.

Yet another object is to provide an expandable intervertebral fusion implant which can be expanded in situ laterally, vertically and longitudinally.

Another object is to provide an expandable intervertebral fusion implant that is both simple to manufacture and simple to use in daily clinical surgical practice while remaining versatile enough to address the complex biologic and pathologic variability of the human spine.

These, and other objects and advantages, will be readily appreciable from the following description of preferred embodiments and from the accompanying drawings and claims.

BRIEF DESCRIPTION OF THE SEVERAL VIEWS OF THE DRAWINGS

The nature and mode of operation of the present disclosure will now be more fully described in the following detailed description of the embodiments taken with the accompanying figures, in which:

FIG. 16A is a perspective view of an expandable intervertebral fusion implant, in an unexpanded state having an intermediate telescoping strut;

FIG. 22A is a side view of a hingedly expandable intervertebral fusion implant, in an unexpanded state;

FIG. 22B is a front view of a hingedly expandable intervertebral fusion implant, in an unexpanded state;

FIG. 22C is a front view of a hingedly expandable intervertebral fusion implant, in an expanded state;

FIG. 22D is a cross-sectional view of a hingedly expandable intervertebral fusion implant in FIG. 22A, in an unexpanded state taken along line 22D-22D in FIG. 22B;

FIG. 22E is a cross-sectional view of a hingedly expandable intervertebral fusion implant in FIG. 22A, in an expanded state taken along line 22E-22E in FIG. 22C;

FIG. 22F is a perspective view of a hingedly expandable intervertebral fusion implant, in an expanded state;

FIG. 23A illustrates a hingedly expandable intervertebral fusion implant in place in the disc space, in an unexpanded state;

FIG. 23B illustrates a hingedly expandable intervertebral fusion implant in place in the disc space, in an expanded state;

DETAILED DESCRIPTION OF EMBODIMENTS

At the outset, it should be appreciated that like drawing numbers on different drawing views identify identical, or functionally similar, structural elements. While the embodiments are described with respect to what is presently considered to be the preferred aspects, it is to be understood that the invention as claimed is not limited to the disclosed aspect. The present invention is intended to include various modifications and equivalent arrangements within the spirit and scope of the appended claims.

Furthermore, it is understood that this disclosure is not limited to the particular methodology, materials and modifications described and, as such, may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
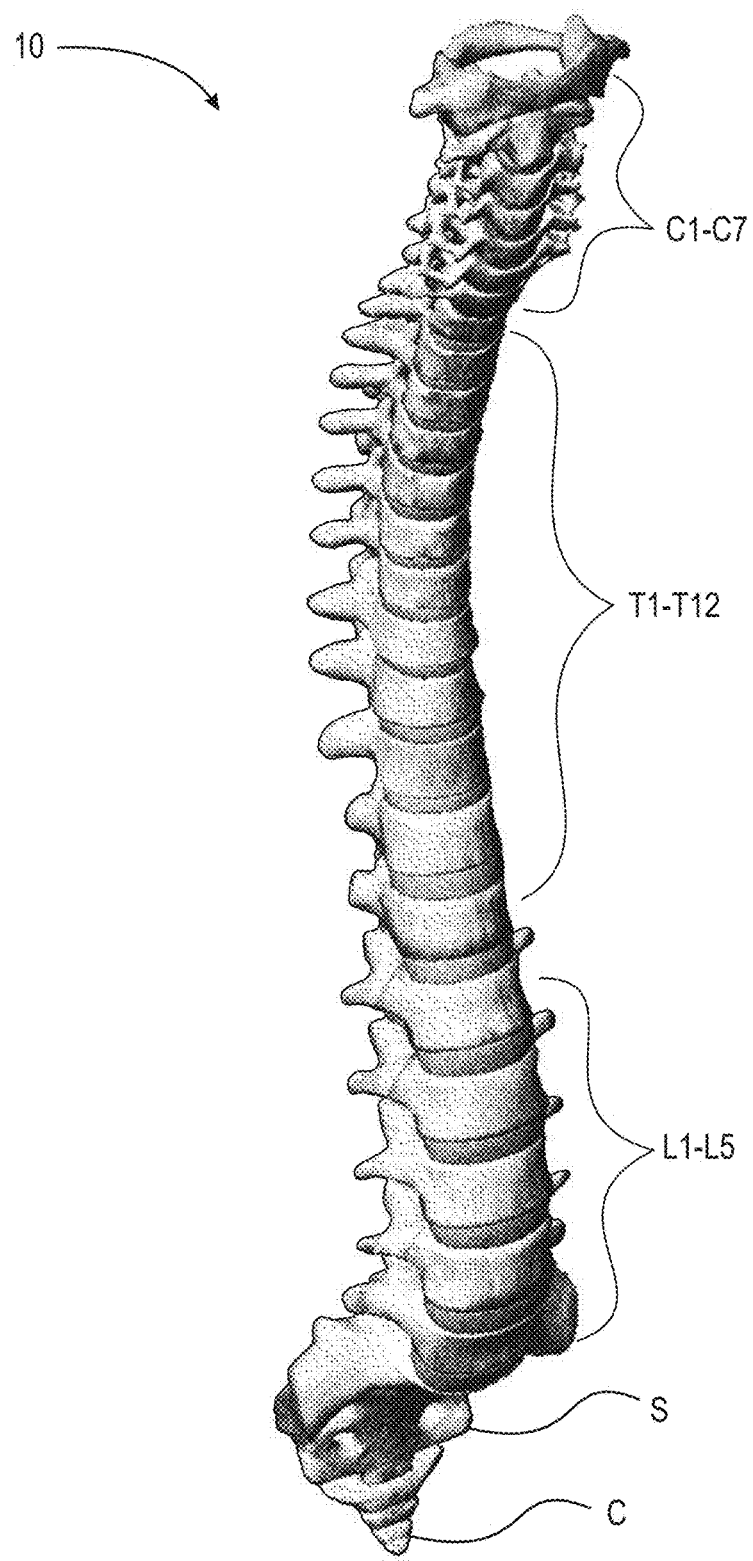
FIG. 1 is an anterior perspective view of spinal column 10.
Figure 2:
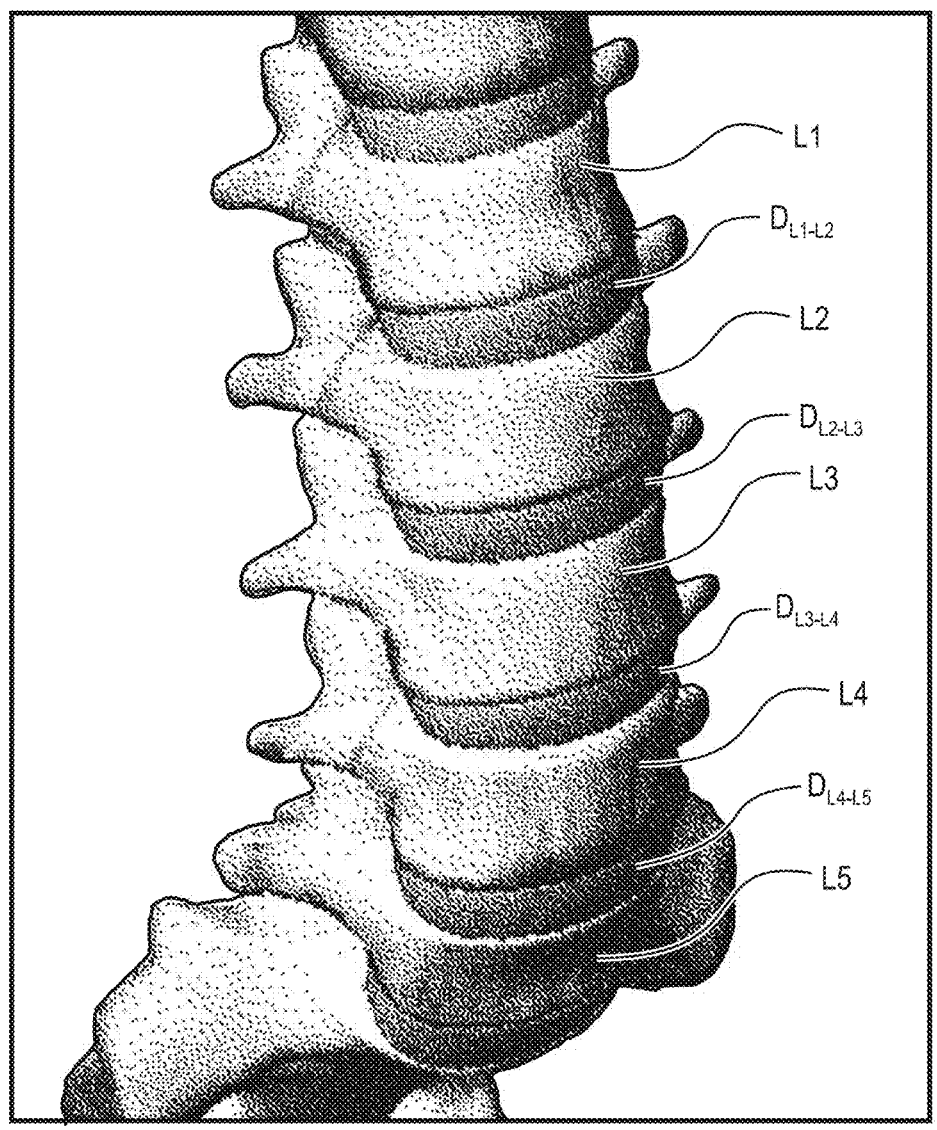
FIG. 2 is an anterior perspective view of the lumbar section of spinal column 10.
Figure 3:
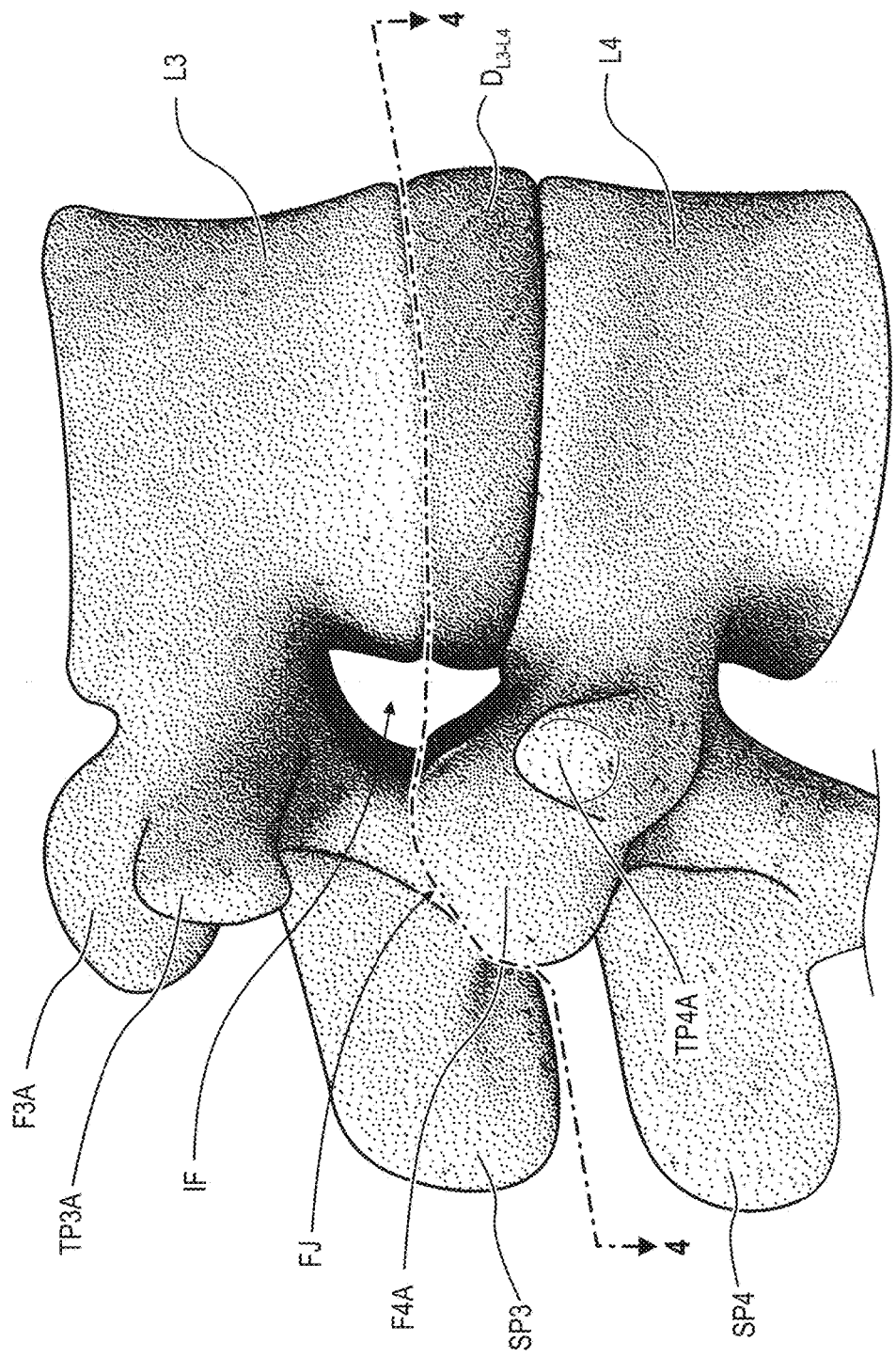
FIG. 3 is a lateral perspective view of L3, L4 vertebrae and disc $D_{L3-L4}$ and related spinal anatomy.
Figure 4:
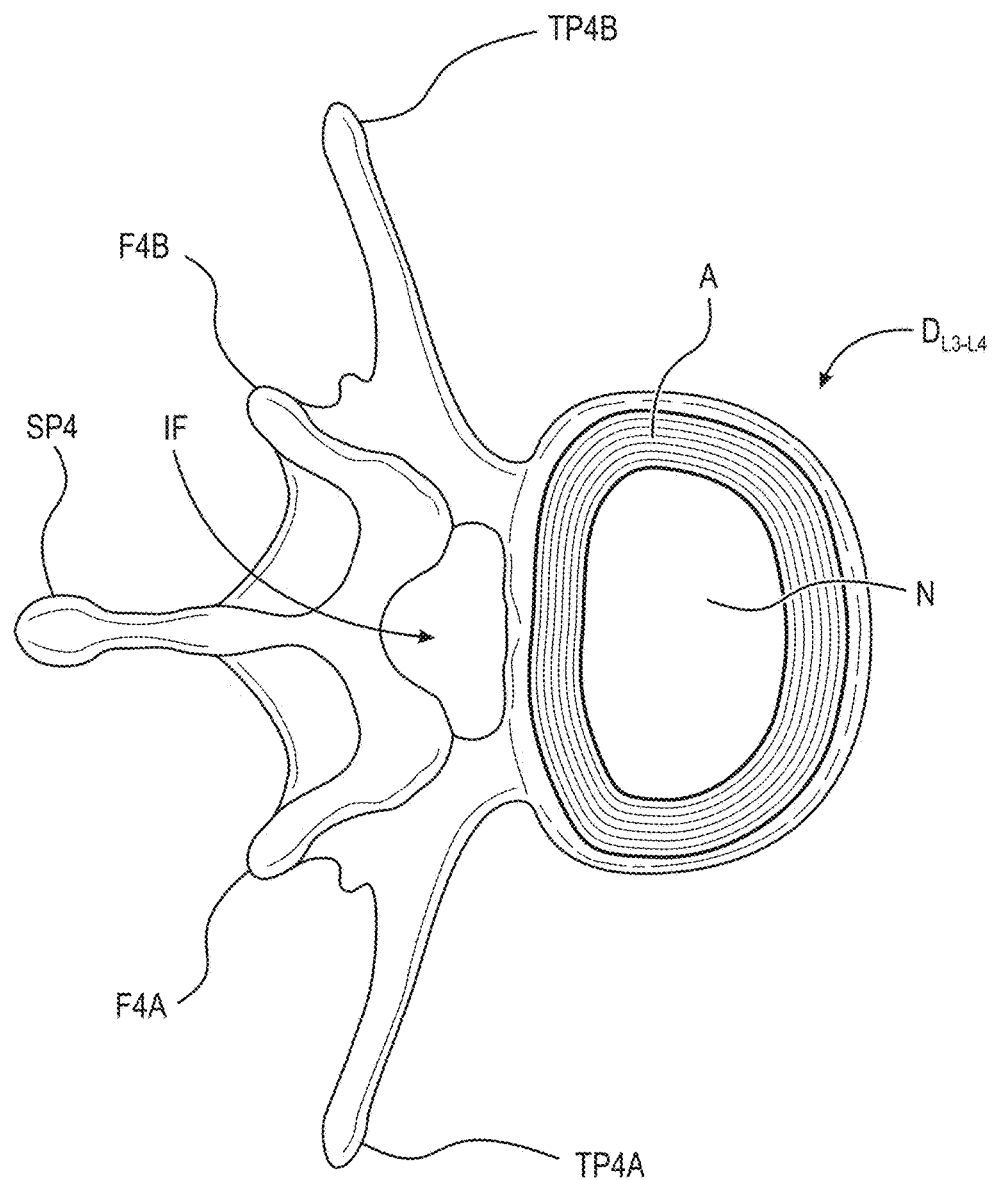
FIG. 4 is a top view of a section of the spinal column, taken generally along line 4-4 in FIG. 3.
Figure 5:
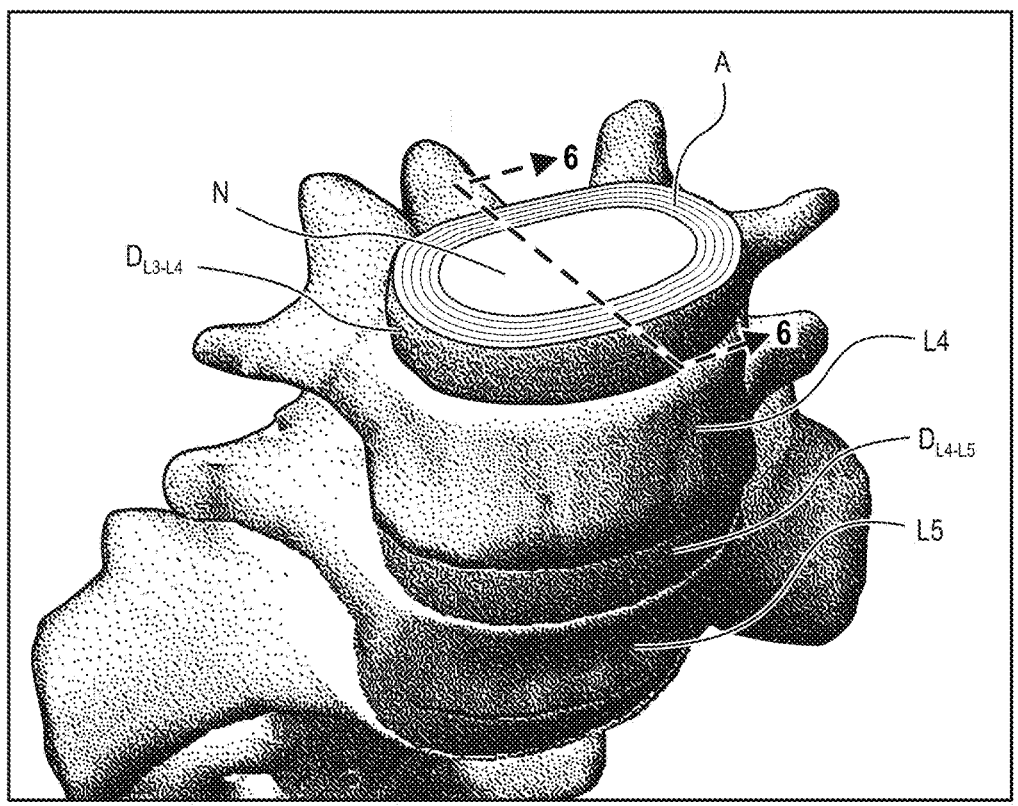
FIG. 5 is an enlarged anterior perspective view of the spinal column shown in FIG. 2, except with vertebra L3 and all other structure above L3 removed.
Figure 6:
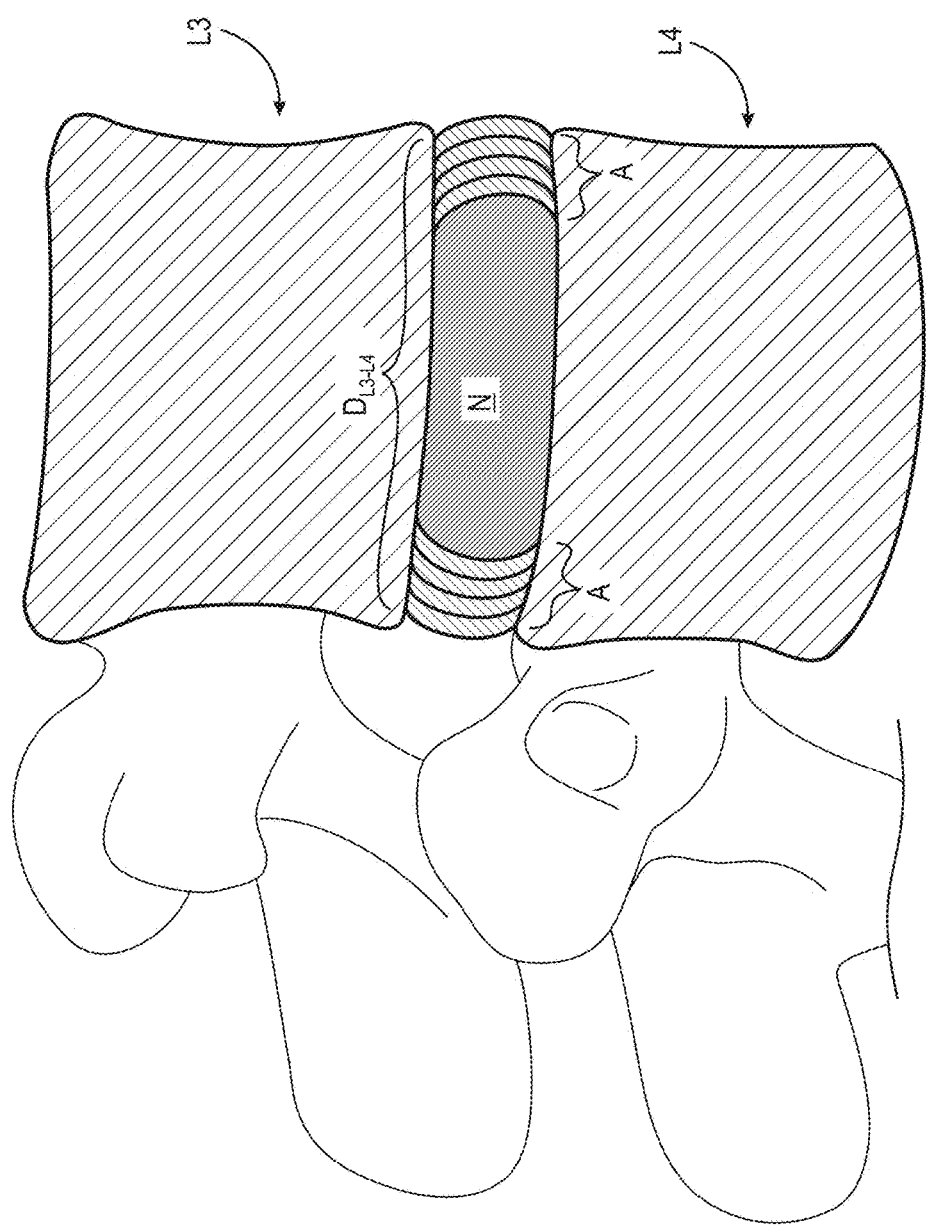
FIG. 6 is a partial cross-sectional view of the L4 vertebra and $D_{L3-L4}$ disc shown in FIG. 5, including L3 in cross-section.
Figure 7:
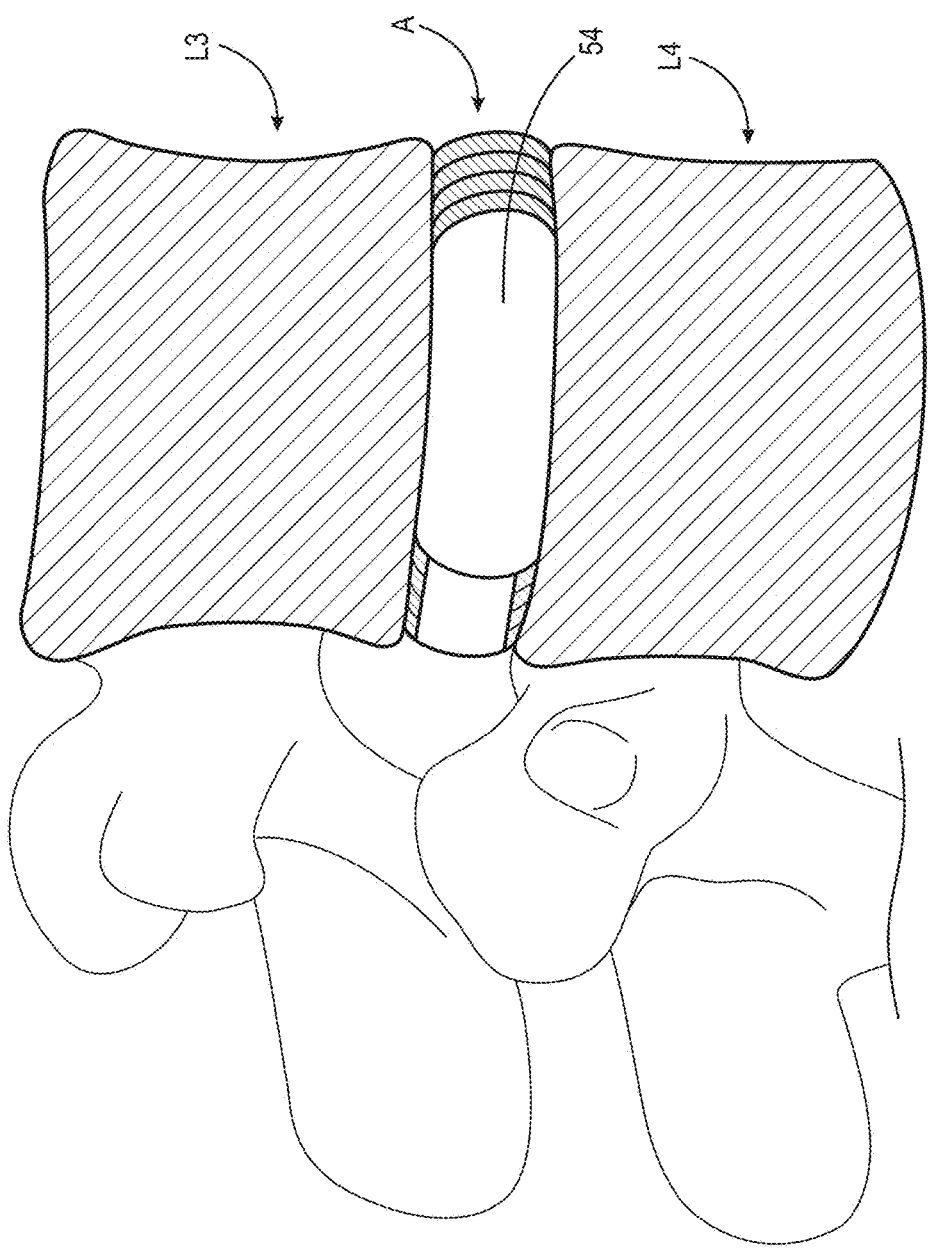
FIG. 7 is a partial cross-sectional view of the L4 vertebra and $D_{L3-L4}$ disc shown in FIG. 5, showing the removal of the disc nucleus post-discectomy.
Figure 8:
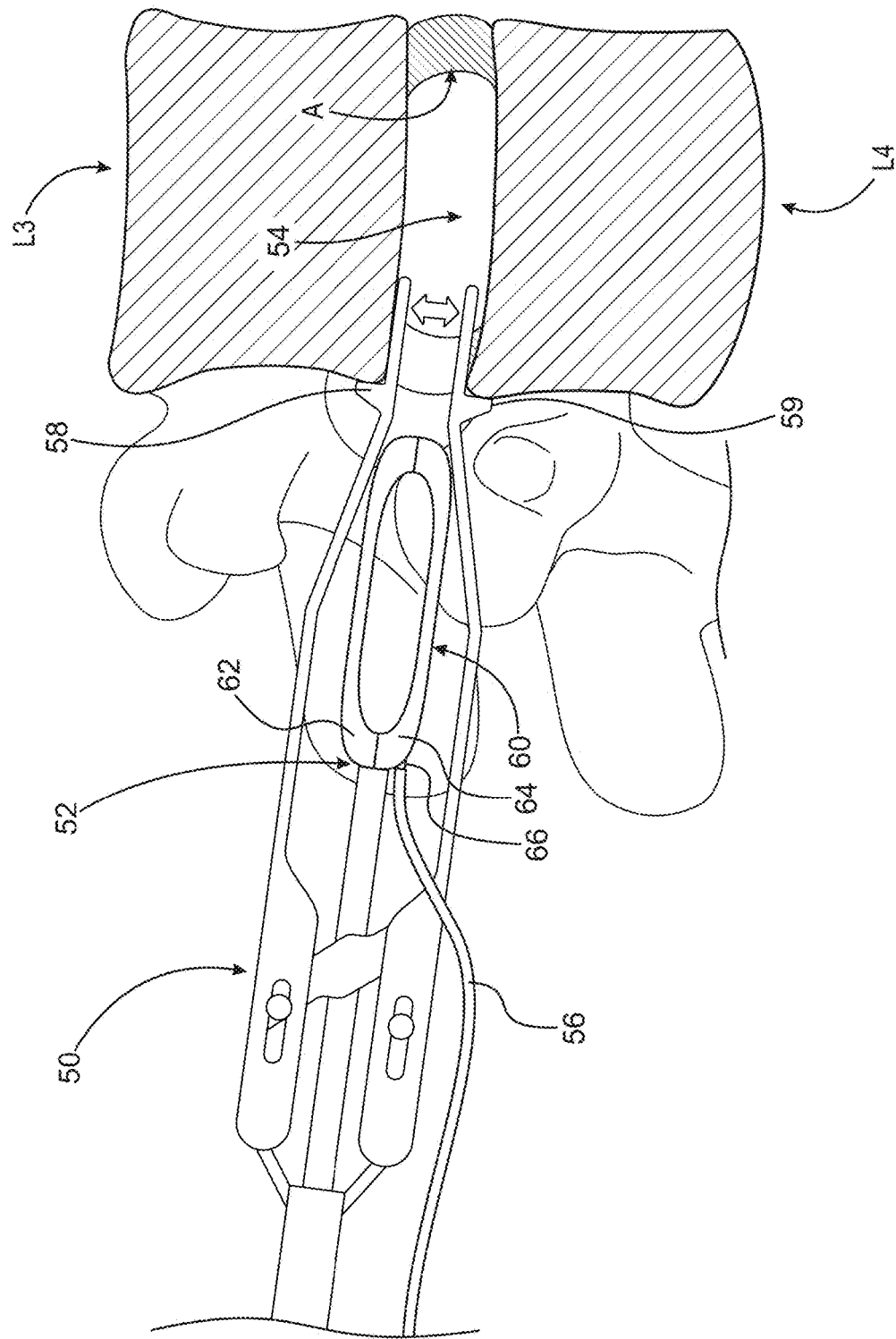
FIG. 8 illustrates a preliminary step in an intervertebral fusion implant procedure, namely, the introduction of a distractor to the disc space.

Adverting now to the Figures, FIG. 8 is a partial cross-sectional view of the L3 and L4 vertebra with disc $D_{L3-L4}$ removed (post discectomy).

Figure 9:
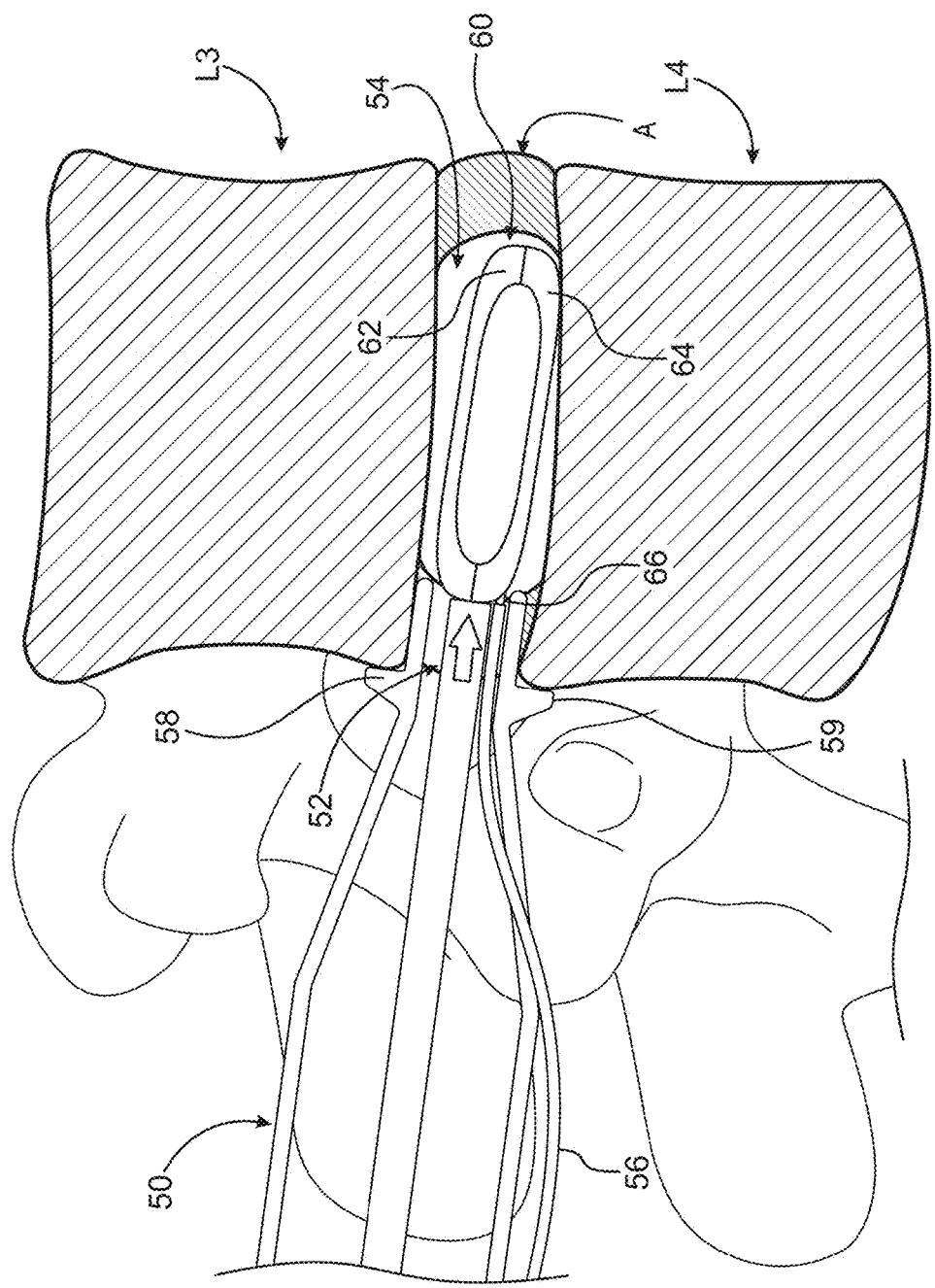
FIG. 9 illustrates the introduction of the intervertebral fusion implant into the disc space using distractor 50 with the implant in an unexpanded state.

FIGS. 8 and 9 illustrate introduction of disc space distractor 50. Distractor 50 is used to maintain distance between vertebrae L3 and L4 and insert expandable intervertebral fusion implant 60 into disc space 54 between the above-mentioned vertebrae. Disc space distractor 50 includes spacers 58 and 59. Spacer 58 is placed between L3 and L4 and contacts the plate of vertebra L3. Spacer 59 is placed between L3 and L4 and contacts the plate of vertebra L4. Spacers 58 and 59 are then separated to enlarge disc space 54. Once disc space 54 is large enough, expandable intervertebral fusion implant 60 may be introduced in an unexpanded state. It should be understood that any suitable tool can be used to maintain distance between the vertebrae and insert the implant.

Figure 10:
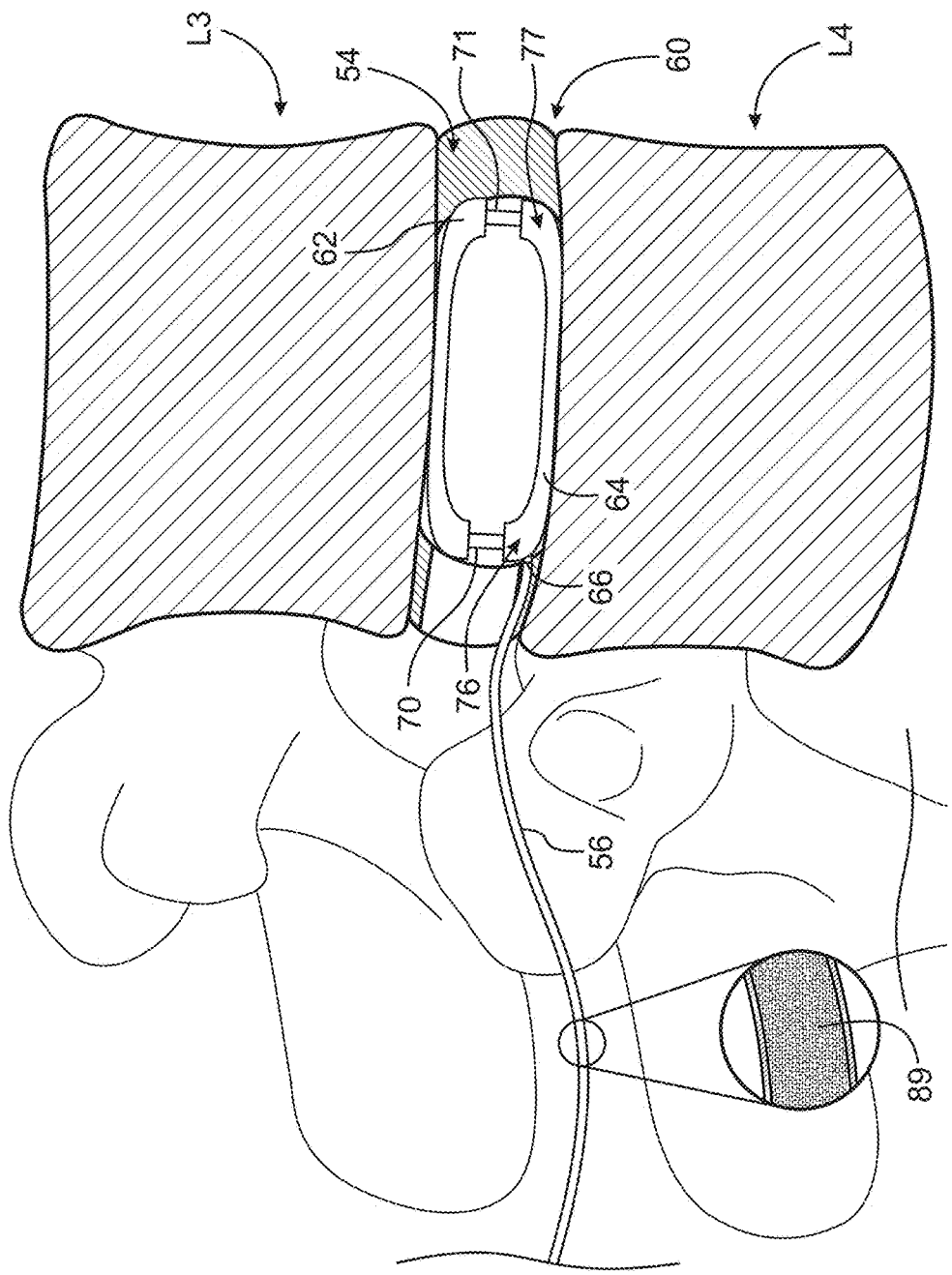
FIG. 10 illustrates the intervertebral fusion implant in place in the disc space, in an expanded state.

FIG. 10 illustrates expandable intervertebral fusion implant 60 in disc space 54, in an expanded state.

Figure 11:
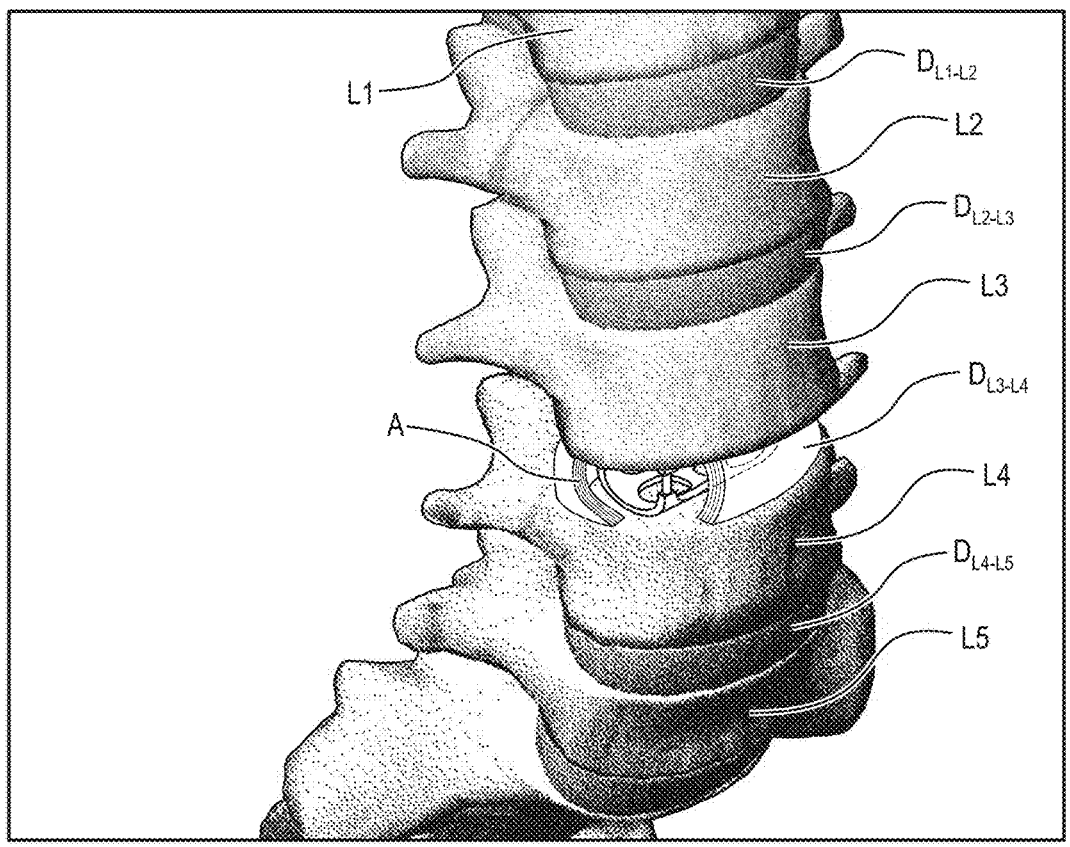
FIG. 11 is an anterior perspective view of spinal column 10 including an expanded intervertebral fusion implant.

FIG. 11 is an anterior perspective view of spinal column 10 including expandable intervertebral fusion implant 60.

Figure 12A:
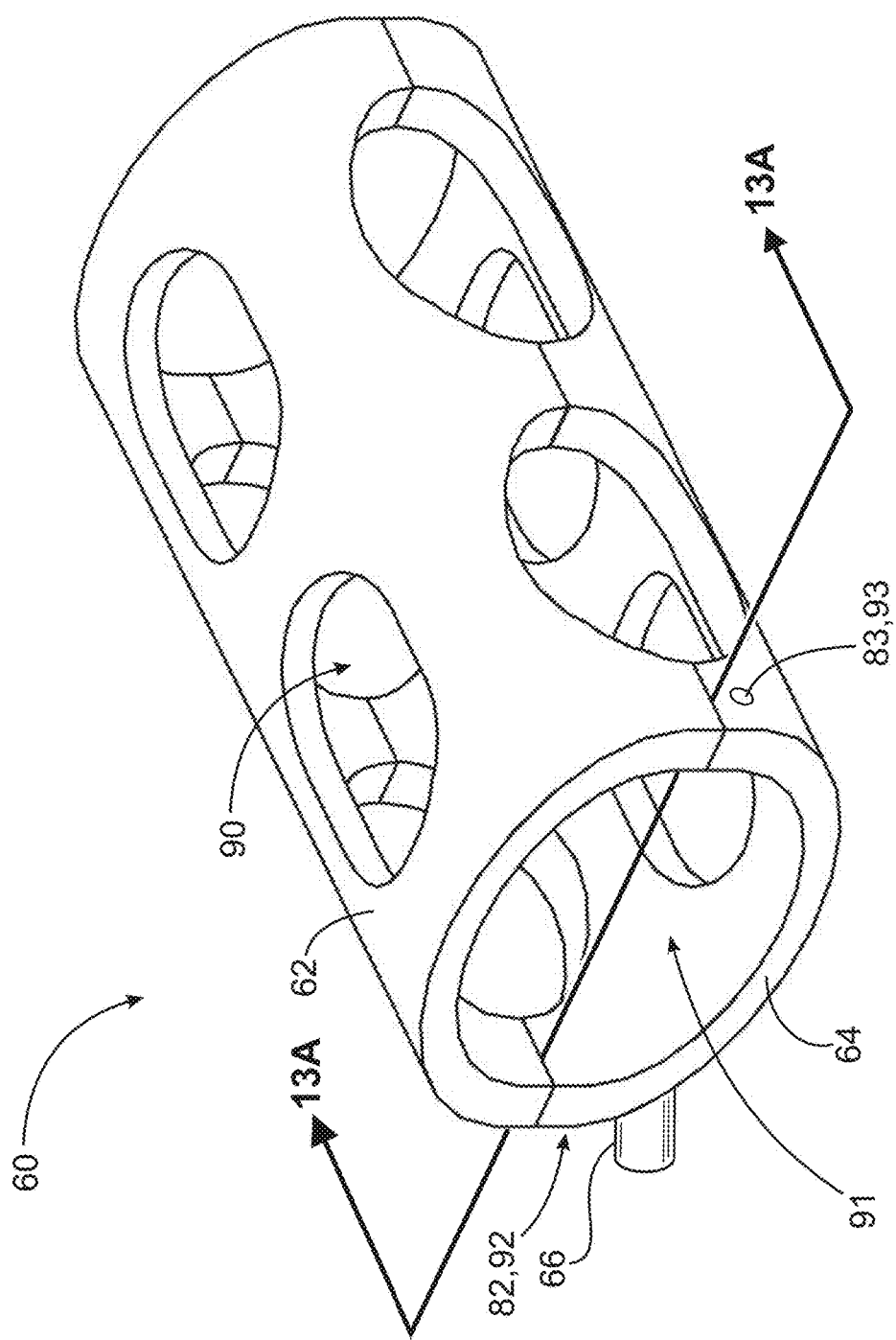
FIG. 12A is a perspective view of an expandable intervertebral fusion implant in an unexpanded state having an input port located on the inferior component.

FIG. 12A is a perspective view of expandable intervertebral fusion implant 60 in an unexpanded state. In the unexpanded state, expandable intervertebral fusion implant 60 comprises superior component 62, inferior component 64, and input port 66. Superior and inferior components 62 and 64 are telescopingly engageable. Superior component 62 comprises a body with a generally arcuate shape (quasi-elliptical cross-section), although implants of other shapes are certainly possible and intended to be within the scope of the appended claims. The body is shown as having at least one aperture 90. Inferior component 64 also comprises a body with an arcuate shape, having at least one aperture 90, and input port 66. The inferior and superior components are of similar shapes and dimensions so as to be capable of matingly engaging one another. When expandable intervertebral fusion implant 60 is in the unexpanded state, superior component 62 and inferior component 64 form a hollow, substantially tubular structure having a cavity 91.

Figure 12B:
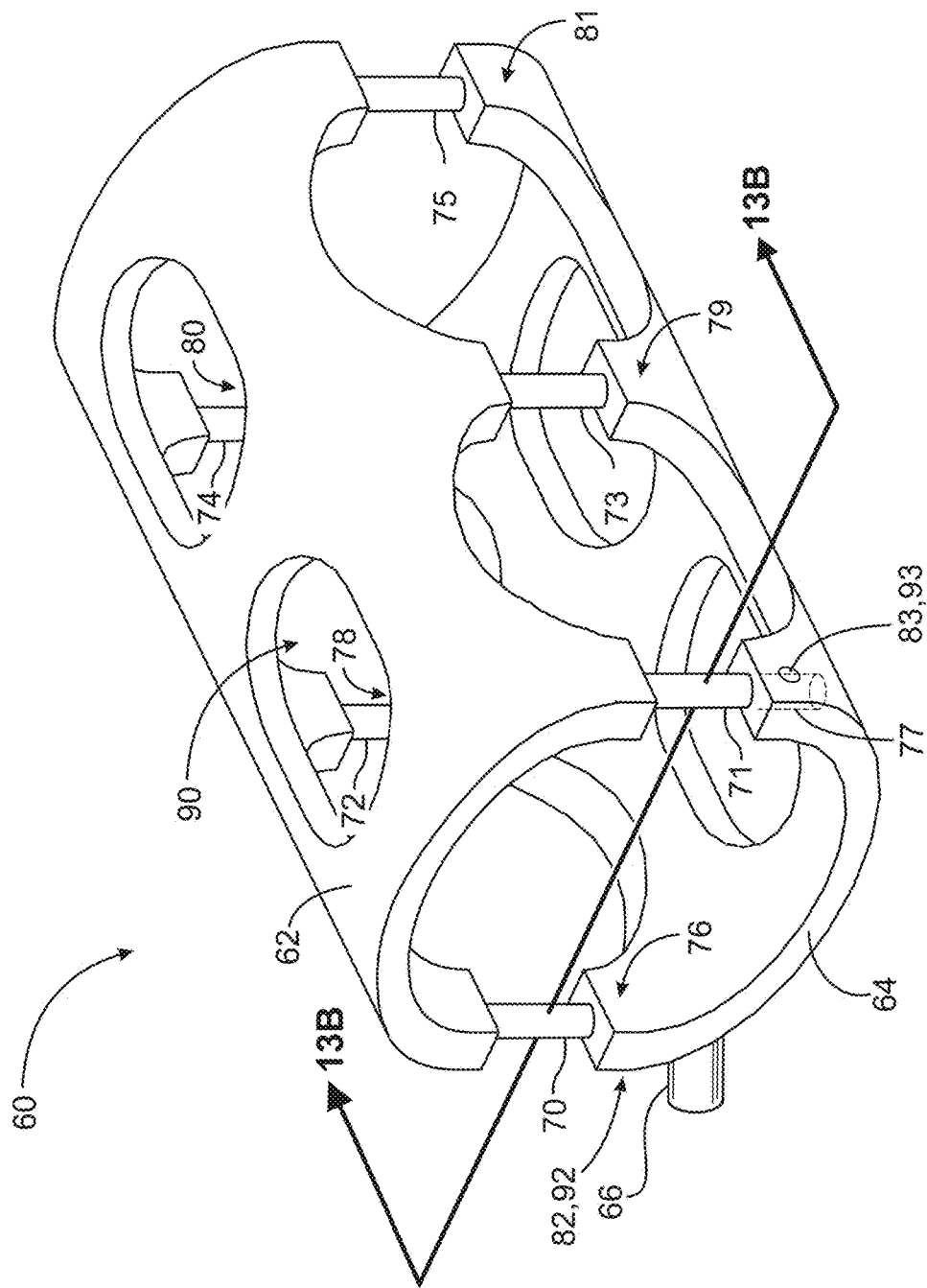
FIG. 12B is a perspective view of an expandable intervertebral fusion implant in an expanded state having an input port located on the inferior component.

FIG. 12B is a perspective view of expandable intervertebral fusion implant 60 in an expanded state. Superior component 62 further comprises a plurality of downwardly extending struts 70, 71, 72, 73, 74 and 75. Inferior component 64 further comprises a plurality of upwardly extending hollow channels 76, 77, 78, 79, 80 and 81 that receive, and telescopingly engage with, downwardly extending struts 70, 71, 72, 73, 74 and 75 respectively. The plurality of upwardly extending hollow channels 76, 77, 78, 79, 80 and 81 are also connected to input port 66. Each hollow channel also includes a vent as described infra.

Figure 13A:
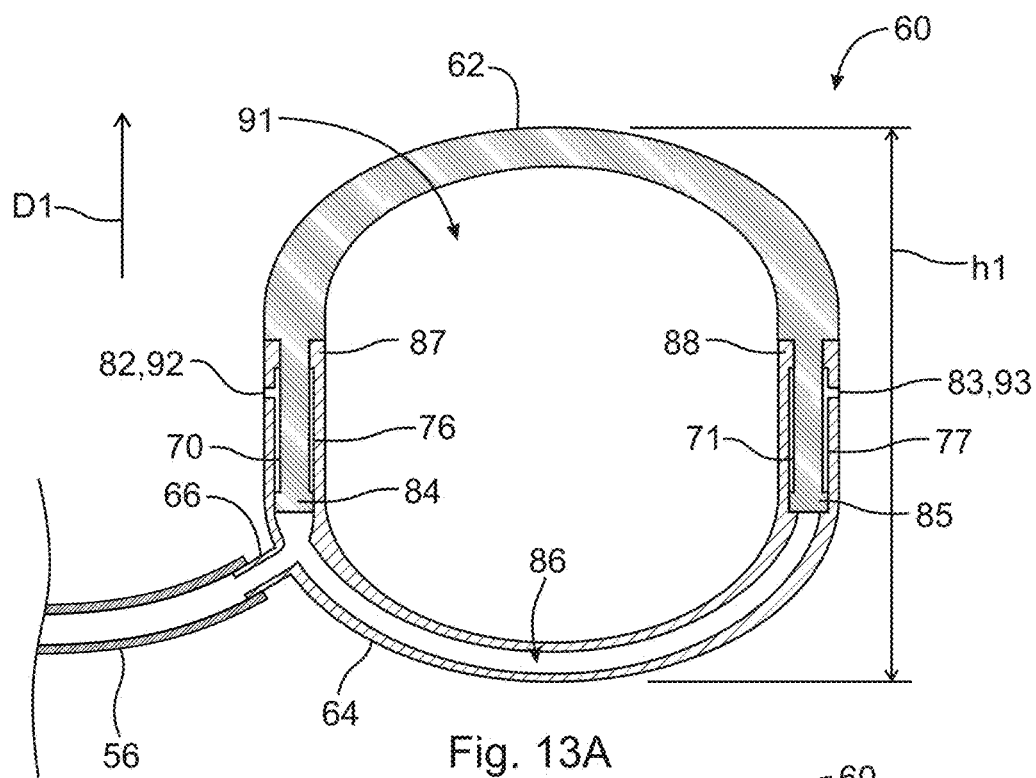
FIG. 13A is a cross-sectional view of an expandable intervertebral fusion implant, in an unexpanded state, taken generally along line 13A-13A in FIG. 12A.

FIG. 13A is a cross-sectional view of an expandable intervertebral fusion implant, in an unexpanded state, taken generally along line 13A-13A in FIG. 12A. Inferior component 64 further comprises channel 86 that connects the plurality of upwardly extending hollow channels 76, 77, 78, 79, 80 and 81. Each of upwardly extending hollow channels 76, 77, 78, 79, 80, and 81 further comprise a retention shoulder operatively arranged to limit movement of the corresponding struts, and prevent the struts from exiting the channels. For example, channel 76 includes shoulder 87 to limit movement of strut 70. Strut 70 includes flange 84 which abuts shoulder 87 when the implant is completely expanded. Similarly, channel 77 includes shoulder 88 to limit movement of strut 71. Strut 71 includes flange 85 which abuts shoulder 88 when the implant is completely expanded.

Figure 13B:
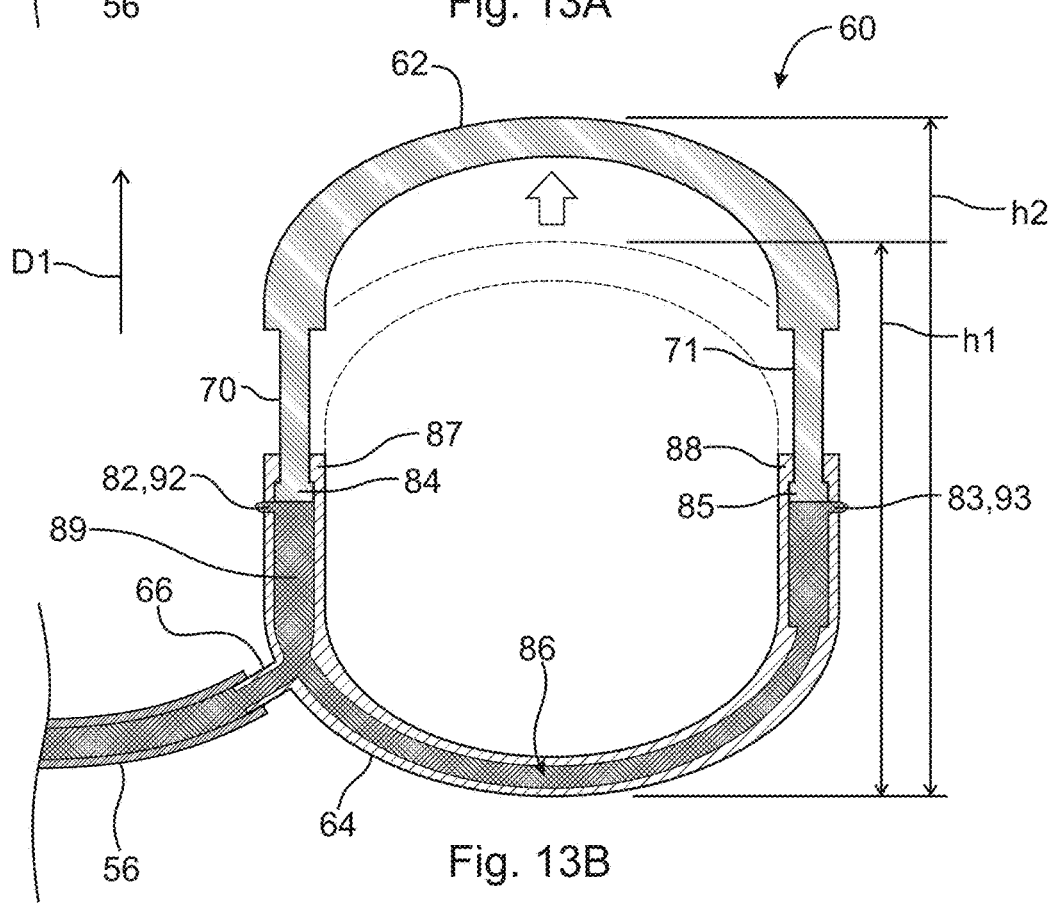
FIG. 13B is a cross-sectional view of an expandable intervertebral fusion implant, in an expanded state, taken generally along line 13B-13B in FIG. 12B.

FIG. 13B is a cross-sectional view of an expandable intervertebral fusion implant, in an expanded state, taken generally along line 13B-13B in FIG. 12B. Hardenable material 89 is injected via input port 66, filling the plurality of upwardly extending hollow channels 76, 77, 78, 79, 80 and 81, as well as channel 86. Injecting hardenable material 89 creates hydraulic pressure within the hollow channels and forces the plurality of downwardly extending struts 70, 71, 72, 73, 74 and 75 in a first direction D1, displacing superior component 62 in a first direction D1.

Each of downwardly extending struts 70, 71, 72, 73, 74 and 75 further comprise a flange operatively arranged to limit movement of each strut within its respective channel. For example, as shown in FIG. 13B, flange 84 of strut 70 is shown abutting shoulder 87, and flange 85 of strut 71 is shown abutting shoulder 88 when the implant is in a fully expanded state. In an unexpanded state, expandable intervertebral fusion implant 60 has a collapsed height $h_1$. As hardenable material 89 is introduced via port 66, and evenly distributed to upwardly extending hollow channels 76, 77, 78, 79, 80 and 81 through channel 86, downwardly extending struts 70, 71, 72, 73, 74 and 75 causing the displacement of superior component 62, in a first direction D1. Upwardly extending hollow channels 76, 77, 78, 79, 80 and 81, as well as channel 86 continue to fill with hardenable material 89, until each flange abuts its respective shoulder, whereby the displacement of superior component 62 is stopped, resulting in expandable intervertebral fusion implant 60 having an expanded height $h_2$. The flanges and shoulder are thus arranged to prevent the struts from being expelled from the channels.

As hardenable material 89 is injected into upwardly extending hollow channels 76, 77, 78, 79, 80 and 81, the air originally contained within the hollow channels as well as channel 86, escapes via vents. For example, channels 76 and 77 each have a vent 82 and 83, respectively. When expandable intervertebral fusion implant 60 is in an expanded state, having expanded height $h_2$, flange 84 is in contact with retention shoulder 87, allowing hardenable material 89 to escape via vent 82. When hardenable material 89 escapes vent 82 instead of air, this signals that the upwardly extending hollow channels have completely filled with hardenable material. (The surgeon can actually see the hardenable material escaping through the vents with an endoscope.) When the surgeon sees the hardenable material escape through the vents, the surgeon is then free to cut injection tube 56 at input port 66, remove the injection tube, and let the hardenable material cure and harden, locking the implant in its expanded state. It should be understood that the vents within each respective hollow channel further contain a valve. For example, vent 82 further comprises valve 83 to allow control of the rate of escaping air and hydraulic pressure within the hollow channels. In the preferred embodiment, hardenable material 89 would be made of poly(methyl methacrylate), polycarbonate resins, epoxy resins, polyamide resins, or equivalent. In the preferred embodiment, superior component 62 and inferior component 64 of expandable intervertebral fusion implant 60 are made of Polyether ether ketone and titanium, or equivalent.

Figure 14A:
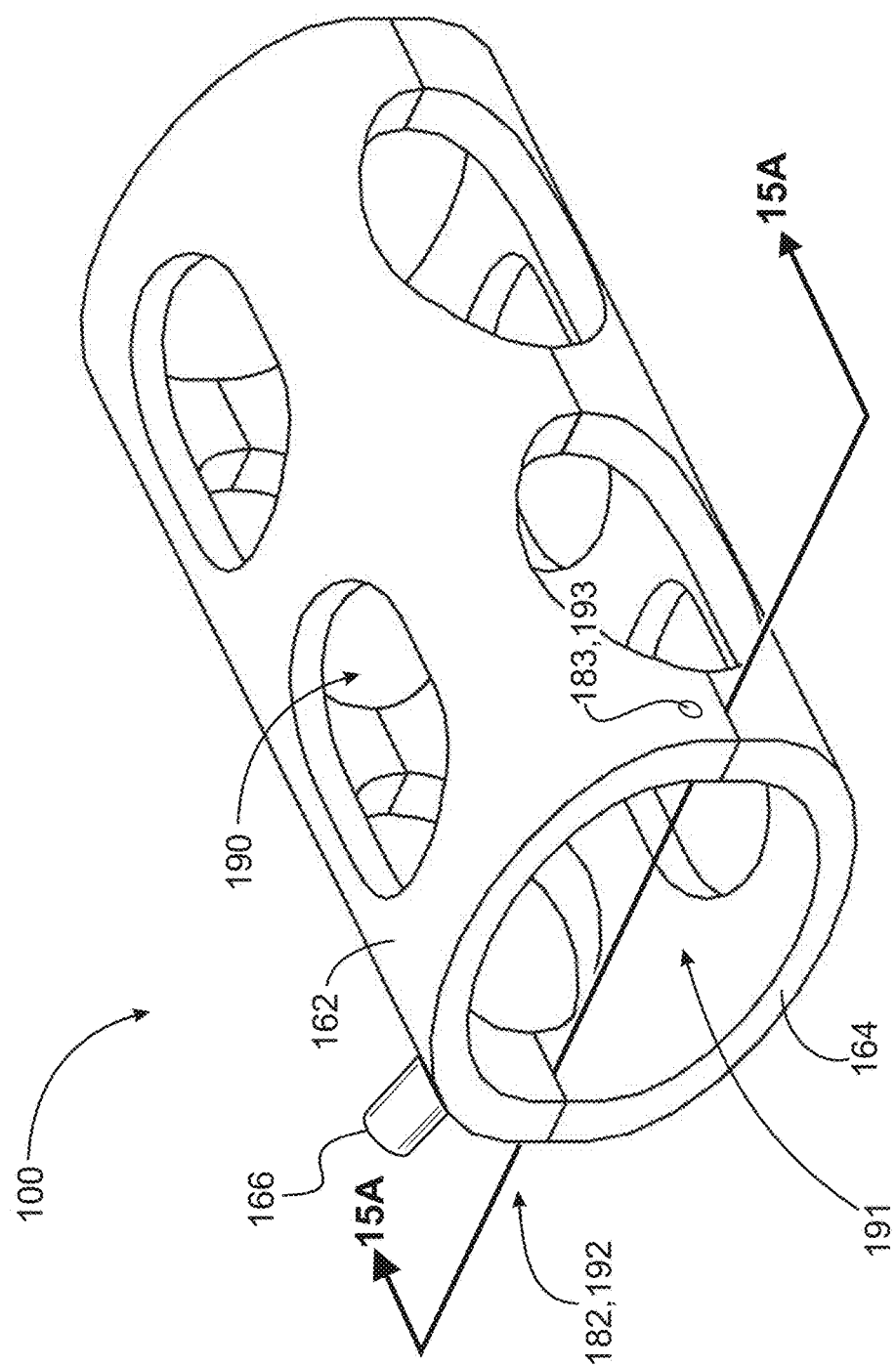
FIG. 14A is a perspective view of an expandable intervertebral fusion implant, in an unexpanded state having an input port located on the superior component.

FIG. 14A is a perspective view of an expandable intervertebral fusion implant 100, comprising superior component 162 and inferior component 164, shown in an unexpanded state. Superior component 162 is shown having input port 166, operatively arranged for import of hardening material into the telescoping struts of the implant. Superior and inferior components 162 and 164 are telescopingly engageable. Superior component 162 comprises a body with a generally arcuate shape (quasi-elliptical cross-section), although implants of other shapes are certainly possible and intended to be within the scope of the appended claims. The body is shown as having at least one aperture 190. Inferior component 164 also comprises a body with an arcuate shape, having at least one aperture 190, and input port 166. The inferior and superior components are of similar shapes and dimensions so as to be capable of matingly engaging one another. When expandable intervertebral fusion implant 100 is in the unexpanded state, superior component 162 and inferior component 164 form a hollow, substantially tubular structure having a cavity 191.

Figure 14B:
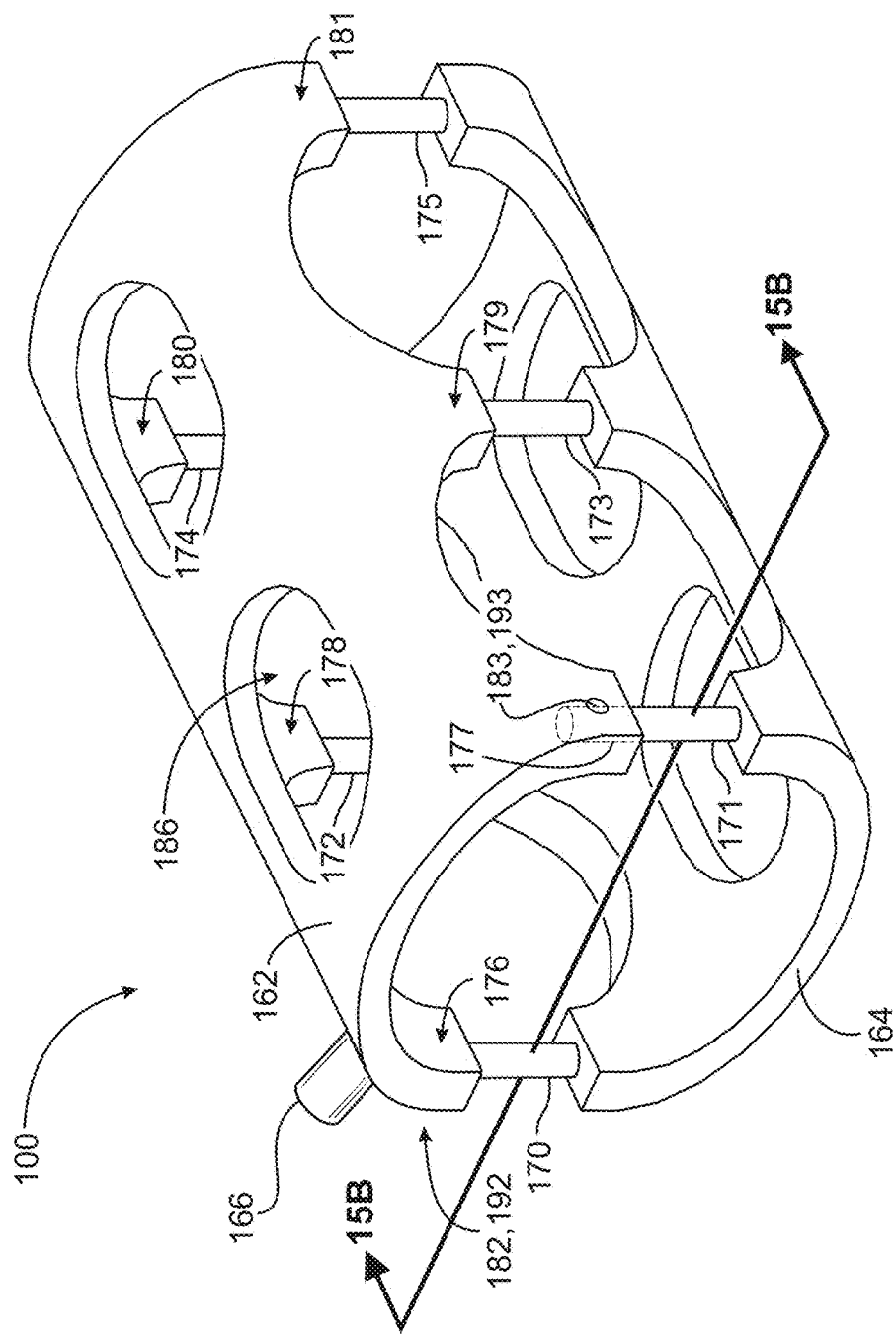
FIG. 14B is a perspective view of an expandable intervertebral fusion implant, in an expanded state having an input port located on the superior component.

FIG. 14B is a perspective view of expandable intervertebral fusion implant 100, in an expanded state. Inferior component 164 further comprises a plurality of upwardly extending struts 170, 171, 172, 173, 174 and 175. Superior component 162 further comprises a plurality of downwardly extending hollow channels 176, 177, 178, 179, 180 and 181 that receive, and telescopingly engage with, upwardly extending struts 170, 171, 172, 173, 174 and 175 respectively. The plurality of downwardly extending hollow channels 176, 177, 178, 179, 180 and 181 are also connected to input port 166. Each hollow channel also includes a vent described infra.

Figure 15A:
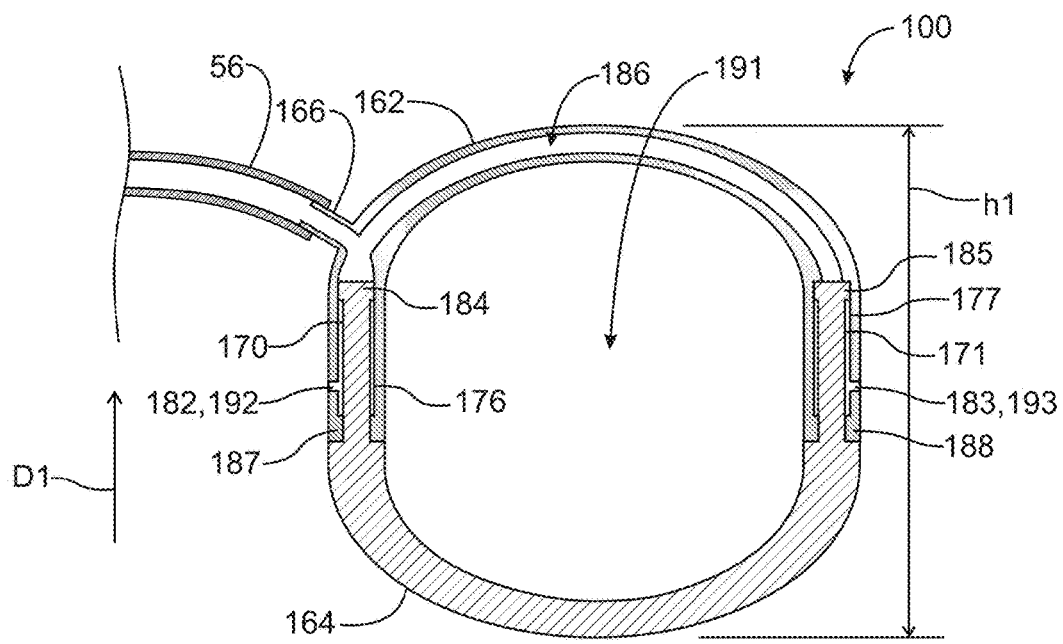
FIG. 15A is a cross-sectional view of an expandable intervertebral fusion implant, in an unexpanded state taken generally along line 15A-15A in FIG. 14A.

FIG. 15A is a cross-sectional view of an expandable intervertebral fusion implant 100, in an unexpanded state taken generally along line 15A-15A in FIG. 14A. Superior component 162 further comprises channel 186 that connects the plurality of downwardly extending hollow channels 176, 177, 178, 179, 180 and 181. Each of downwardly extending hollow channels 176, 177, 178, 179, 180 and 181 further comprises a retention shoulder operatively arranged to limit movement of the corresponding struts, and prevent the struts from exiting the channels. For example, channel 176 includes shoulder 187 to limit movement of strut 170. Strut 170 includes flange 184 which abuts shoulder 187 when the implant is completely expanded. Similarly, channel 177 includes shoulder 188 to limit movement of strut 171. Strut 171 includes flange 185 which abuts shoulder 188 when the implant is completely expanded.

Figure 15B:
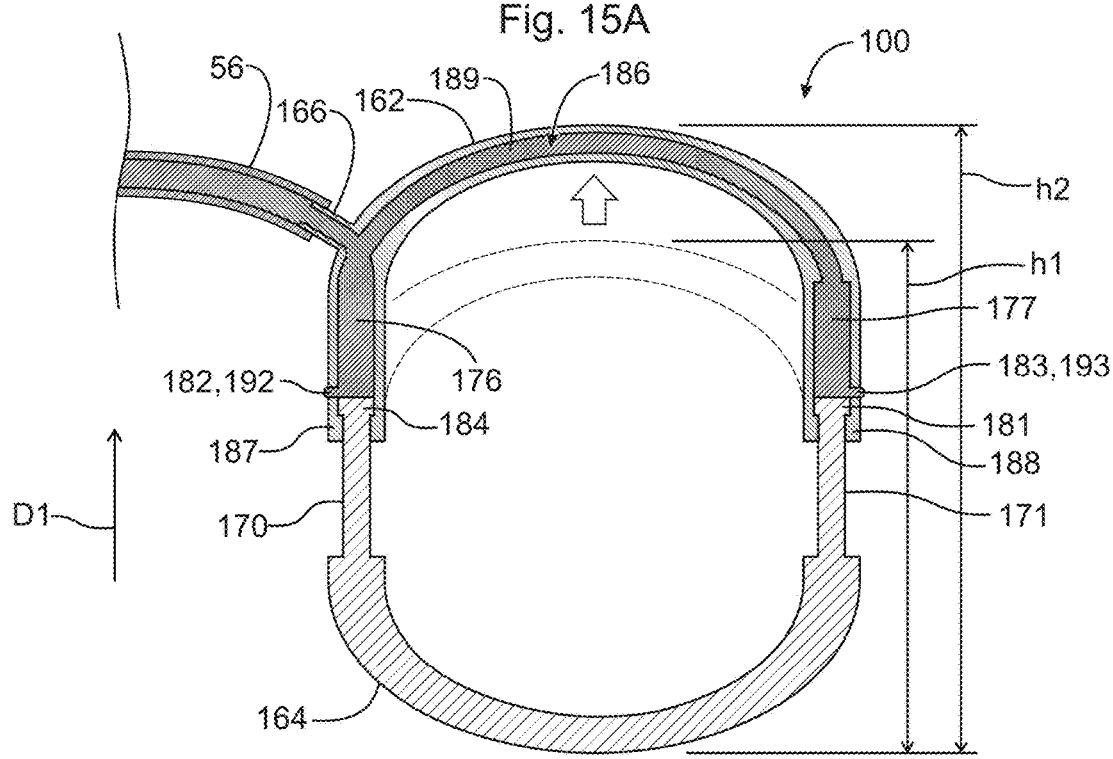
FIG. 15B is a cross-sectional view of an expandable intervertebral fusion implant, in an expanded state taken generally along line 15B-15B in FIG. 14B.

FIG. 15B is a cross-sectional view of an expandable intervertebral fusion implant 100, in an expanded state taken generally along line 15B-15B in FIG. 14B. Hardenable material 189 is injected via input port 166, filling the plurality of downwardly extending hollow channels 176, 177, 178, 179, 180 and 181, as well as channel 186. Injecting hardenable material 189 creates hydraulic pressure within the hollow channels and forces the plurality of upwardly extending struts 170, 171, 172, 173, 174 and 175 in a first direction D1, displacing superior component 162 in a first direction D1.

Each of the upwardly extending struts 170, 171, 172, 173, 174 and 175 further comprise a flange operatively arranged to limit movement of each strut within its respective channel. For example, as shown in FIG. 15B, flange 184 of strut 170 is shown abutting shoulder 187, and flange 185 of strut 171 is shown abutting shoulder 188 when the implant is in a fully expanded state. In an unexpanded state, expandable intervertebral fusion implant 100 has a collapsed height $h_1$ (as shown in FIG. 15A). As hardenable material 189 is introduced via port 166, and evenly distributed to downwardly extending hollow channels 176, 177, 178, 179, 180 and 181 through channel 186, upwardly extending struts 170, 171, 172, 173, 174 and 175 causing the displacement of superior component 162, in a first direction D1. Downwardly extending hollow channels 176, 177, 178, 179, 180 and 181, as well as channel 186 continue to fill with hardenable material 189, until each flange abuts its respective shoulder, whereby the displacement of superior component 162 is stopped, resulting in expandable intervertebral fusion implant 100 having an expanded height $h_2$ (as shown in FIG. 15B). The flanges and shoulder are thus arranged to prevent the struts from being expelled from the channels.

As hardenable material 189 is injected into downwardly extending hollow channels 176, 177, 178, 179, 180 and 181, the air originally contained within the hollow channels as well as channel 186, escapes via vents. Each channel has a vent, although only two of the six vents are shown for illustration in the drawings. For example, channels 176 and 177 each have a vent 182 and 183, respectively. When expandable intervertebral fusion implant 100 is in an expanded state, having expanded height $h_2$, flange 184 is in contact with retention shoulder 187, allowing hardenable material 189 to escape via vent 182. When hardenable material 189 escapes vent 182 instead of air, this signals that the downwardly extending hollow channels 176, 177, 178, 179, 180 and 181, have completely filled with hardenable material 80. (The surgeon can actually see the hardenable material escaping through the vents with an endoscope.) When the surgeon sees the hardenable material escape through the vents, the surgeon is then free to cut injection tube 56 at input port 166, remove the injection tube and let the hardenable material cure and harden, locking the implant in its expanded state. It should be understood that the vents within each respective hollow channel further contain a valve. For example, vent 182 further comprises valve 183 to allow control of the rate of escaping air and hydraulic pressure within the hollow channels. Hardenable material 189 is preferably made of poly(methyl methacrylate), polycarbonate resins, epoxy resins, polyamide resins, or equivalent. Superior component 162 and inferior component 164 of expandable intervertebral fusion implant 100 are preferably made of polyether ether ketone and titanium, or equivalent.

FIG. 16A is a perspective view of expandable intervertebral fusion implant 200, in an unexpanded state having an intermediate telescoping struts 220, 221, 222, 223, 224 and 225. Expandable intervertebral fusion implant 200 comprises superior component 262, inferior component 264, and input port 266. Superior and inferior components 262 and 264 are telescopingly engagable. Superior component 262 comprises a body with a generally arcuate shape (quasi-elliptical cross-section), although implants of other shapes are certainly possible and intended to be within the scope of the appended claims. The body is shown as having at least one aperture 290. Inferior component 264 comprises a body with an arcuate shape, having at least one aperture 286, and input port 266. The inferior and superior components are of similar shapes and dimensions so as to be capable of matingly engaging one another. When expandable intervertebral fusion implant 200 is in the unexpanded state, superior component 262 and inferior component 264 form a hollow, substantially tubular structure having a cavity 291.

Figure 16B:
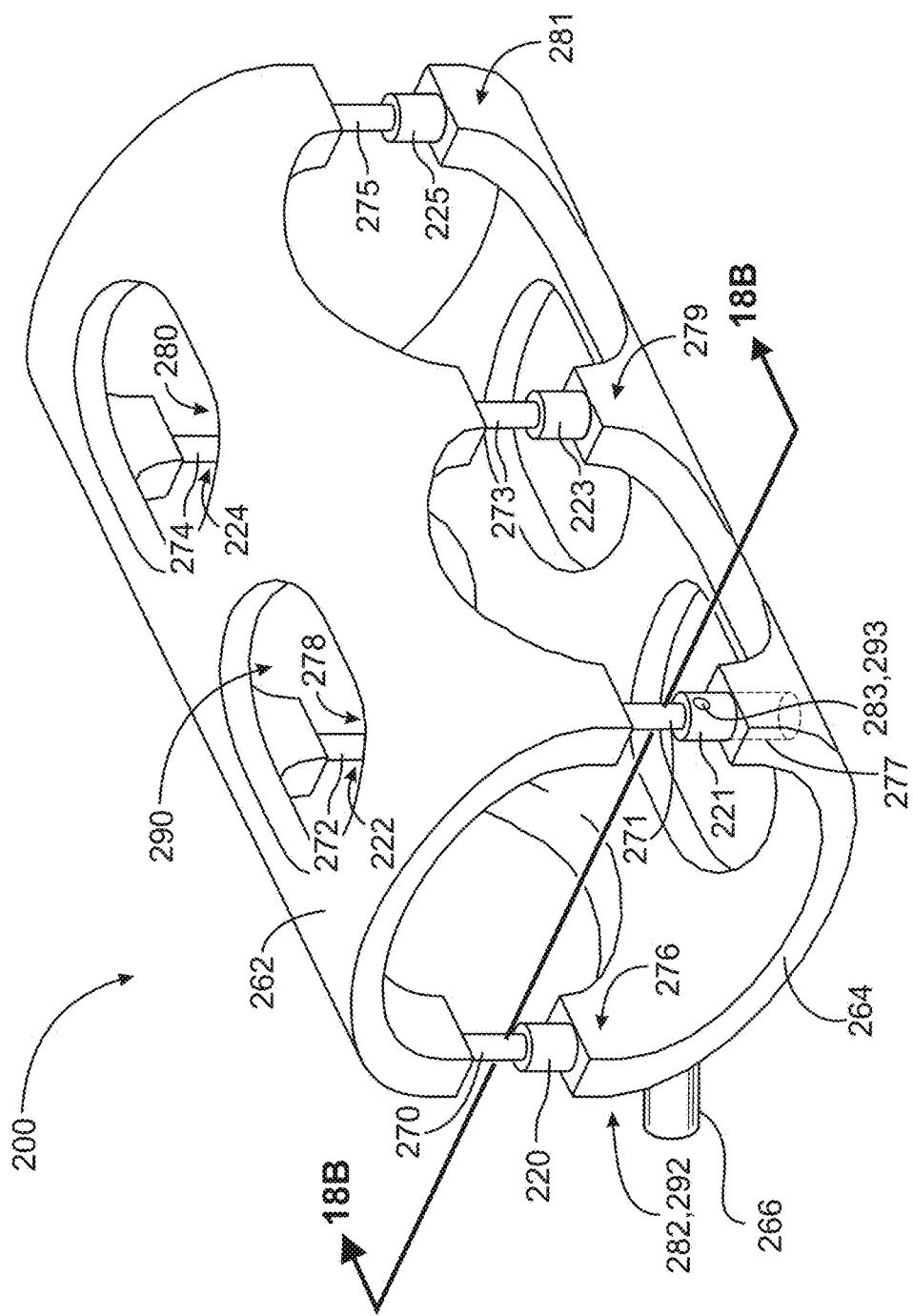
FIG. 16B is a perspective view of an expandable intervertebral fusion implant, in an expanded state having an intermediate telescoping strut.

FIG. 16B is a perspective view of expandable intervertebral fusion implant 200, in an unexpanded state having intermediate telescoping struts 220, 221, 222, 223, 224 and 225. Superior component 262 further comprises a plurality of downwardly extending struts 270, 271, 272, 273, 274 and 275. Inferior component 264 further comprises a plurality of upwardly extending hollow channels 276, 277, 278, 279, 280 and 281 that receive, and telescopingly engage with, intermediate telescoping struts 220, 221, 222, 223, 224 and 225 respectively. Intermediate telescoping struts 220, 221, 222, 223, 224 and 225 receive and telescopingly engage with downwardly extending struts 270, 271, 272, 273, 274 and 275 respectively. The plurality of upwardly extending hollow channels 276, 277, 278, 279, 280 and 281 are also connected to input port 266. Intermediate telescoping strut also includes a vent described infra.

Figure 17A:
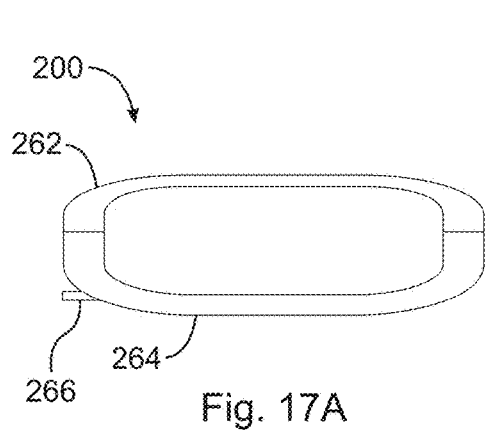
FIG. 17A is a front view of an expandable intervertebral fusion implant, in an unexpanded state having an intermediate telescoping strut.

FIG. 17A is a front view of an expandable intervertebral fusion implant 200, in an unexpanded state having intermediate telescoping struts 220, 221, 222, 223, 224 and 225.

Figure 17B:
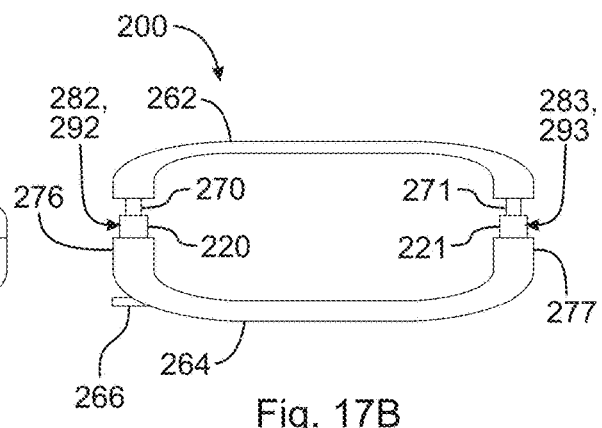
FIG. 17B is a front view of an expandable intervertebral fusion implant, in an expanded state having an intermediate telescoping strut.

FIG. 17B is a front view of an expandable intervertebral fusion implant 200, in an expanded state having intermediate telescoping struts 220, 221, 222, 223, 224 and 225. In this view only struts 220, 270, 221 and 271 are shown.

Figure 18A:
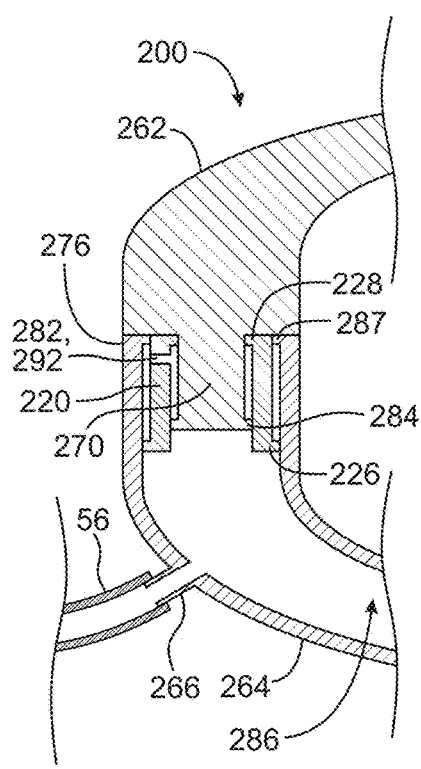
FIG. 18A is a partial cross-sectional view of an expandable intervertebral fusion implant in FIG. 17A, in an unexpanded state taken generally along line 18A-18A in FIG. 16A.

FIG. 18A a partial cross-sectional view of an expandable intervertebral fusion implant 200 in FIG. 17A, in an unexpanded state taken generally along line 18A-18A in FIG. 16A having intermediate telescoping struts 220, 221, 222, 223, 224 and 225. Inferior component 264 further comprises channel 286 that connects the plurality of upwardly extending hollow channels 276, 277, 278, 279, 280 and 281. Each of upwardly extending hollow channels 276, 277, 278, 279, 280 and 281 further comprises intermediate telescoping struts 220, 221, 222, 223, 224 and 225, respectively. Each intermediate telescoping strut 220, 221, 222, 223, 224 and 225 further comprises an intermediate retention shoulder, an intermediate flange, and a vent respectively. (Only one of the six intermediate retention shoulders, 228, one of the six intermediate flanges, 226, and one of the vents, 282, are shown in the drawings.)

Figure 18B:
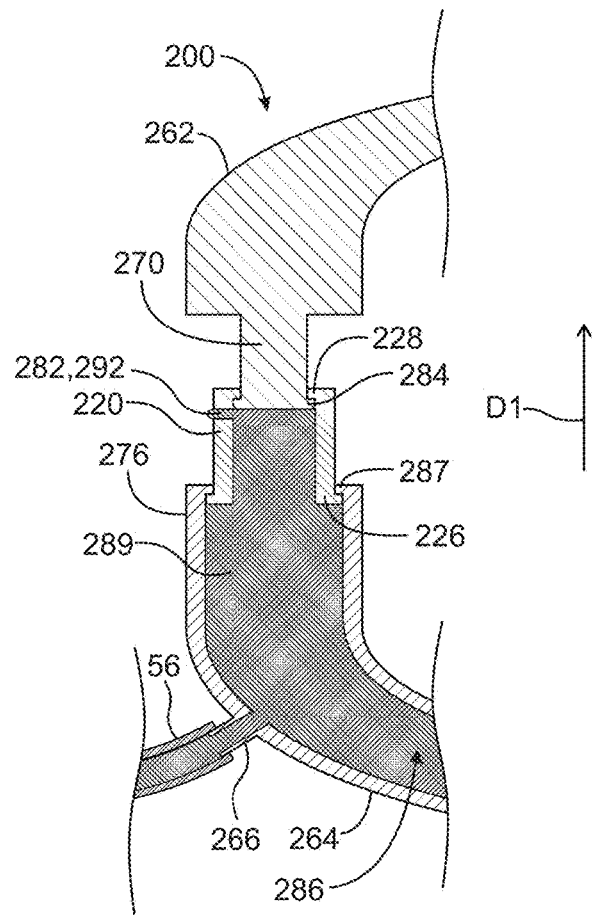
FIG. 18B is a partial cross-sectional view of an expandable intervertebral fusion implant in FIG. 17B, in an expanded state taken generally along line 18B-18B in FIG. 16B.

FIG. 18B is a partial cross-sectional view of an expandable intervertebral fusion implant 200 in FIG. 17B, in an expanded state taken generally along line 18B-18B in FIG. 16B. Hardenable material 289 is injected via input port 266, filling the plurality of upwardly extending hollow channels 276, 277, 278, 279, 280 and 281, as well as channel 286. Injecting hardenable material 289 creates hydraulic pressure within the hollow channels and forces the plurality of downwardly extending struts 270, 271, 272, 273, 274 and 275 in a first direction D1, displacing superior component 262 in a first direction D1.

Each of downwardly extending struts 270, 271, 272, 273, 274 and 275 further comprises a flange operatively arranged to limit movement of each intermediate strut within its respective channel. For example, as shown in FIG. 18B, flange 284 is shown abutting intermediate flange 227 when expandable intervertebral fusion implant 200 is in a fully expanded state. As hardenable material 289 is introduced via port 266, and evenly distributed to upwardly extending hollow channels 276, 277, 278, 279, 280 and 281, as well as, intermediate telescoping struts 220, 221, 222, 223, 224 and 225 through channel 286, downwardly extending struts 270, 271, 272, 273, 274 and 275, as well as, intermediate telescoping struts 220, 221, 222, 223, 224 and 225 are displaced in a first direction D1, displacing superior component 262, in a first direction D1. The upwardly extending hollow channels 276, 277, 278, 279, 280 and 281, intermediate telescoping struts 220, 221, 222, 223, 224 and 225, and channel 286 continue to fill with hardenable material 289, until each flange of each the downwardly extending struts 270, 271, 272, 273, 274 and 275 contact each respective intermediate retention shoulder of each of intermediate telescoping struts 220, 221, 222, 223, 224 and 225; and, each intermediate flange contacts each retention shoulder of each of the upwardly extending hollow channels 276, 277, 278, 279, 280 and 281, whereby the displacement of superior component 162 in direction D1 is stopped. The flanges and intermediate retention shoulders abut, and the intermediate flanges and shoulders abut, and are thus arranged to prevent the struts and the intermediate struts from being expelled from the channels.

As hardenable material 289 is injected into upwardly extending hollow channels 276, 277, 278, 279, 280 and 281, the air originally contained within the hollow channels, the intermediate telescoping struts, and channel 286, escapes via vents. Each intermediate strut has a vent, although only two of the six vents are shown for illustration in the drawings. For example, intermediate struts 220 and 221 each have a vent 282 and 283 respectively. When expandable intervertebral fusion implant 200 is in an expanded state, flange 284 is in contact with intermediate retention shoulder 227, allowing hardenable material 289 to escape via vent 282. When hardenable material 289 escapes vent 282 instead of air, this signals that the upwardly extending hollow channels 276, 277, 278, 279, 280 and 281, and the intermediate telescoping struts 220, 221, 222, 223, 224 and 225 have completely filled with hardenable material 80. (The surgeon can actually see the hardenable material escaping through the vents with an endoscope.) When the surgeon sees the hardenable material escape through the vents, the surgeon is then free to cut injection tube 56 at input port 266, remove the injection tube, and let the hardenable material cure and harden, locking the implant in its expanded state. It should be understood that the vents within each respective intermediate strut further contain a valve. For example, vent 282 further comprises valve 283 to allow control of the rate of escaping air and hydraulic pressure within the hollow channels and intermediate struts. Hardenable material 289 is preferably made of poly(methyl methacrylate), polycarbonate resins, epoxy resins, polyamide resins, or equivalent. Superior component 262 and inferior component 264 of expandable intervertebral fusion implant 200 are preferably made of polyether ether ketone and titanium, or equivalent.

Figure 19A:
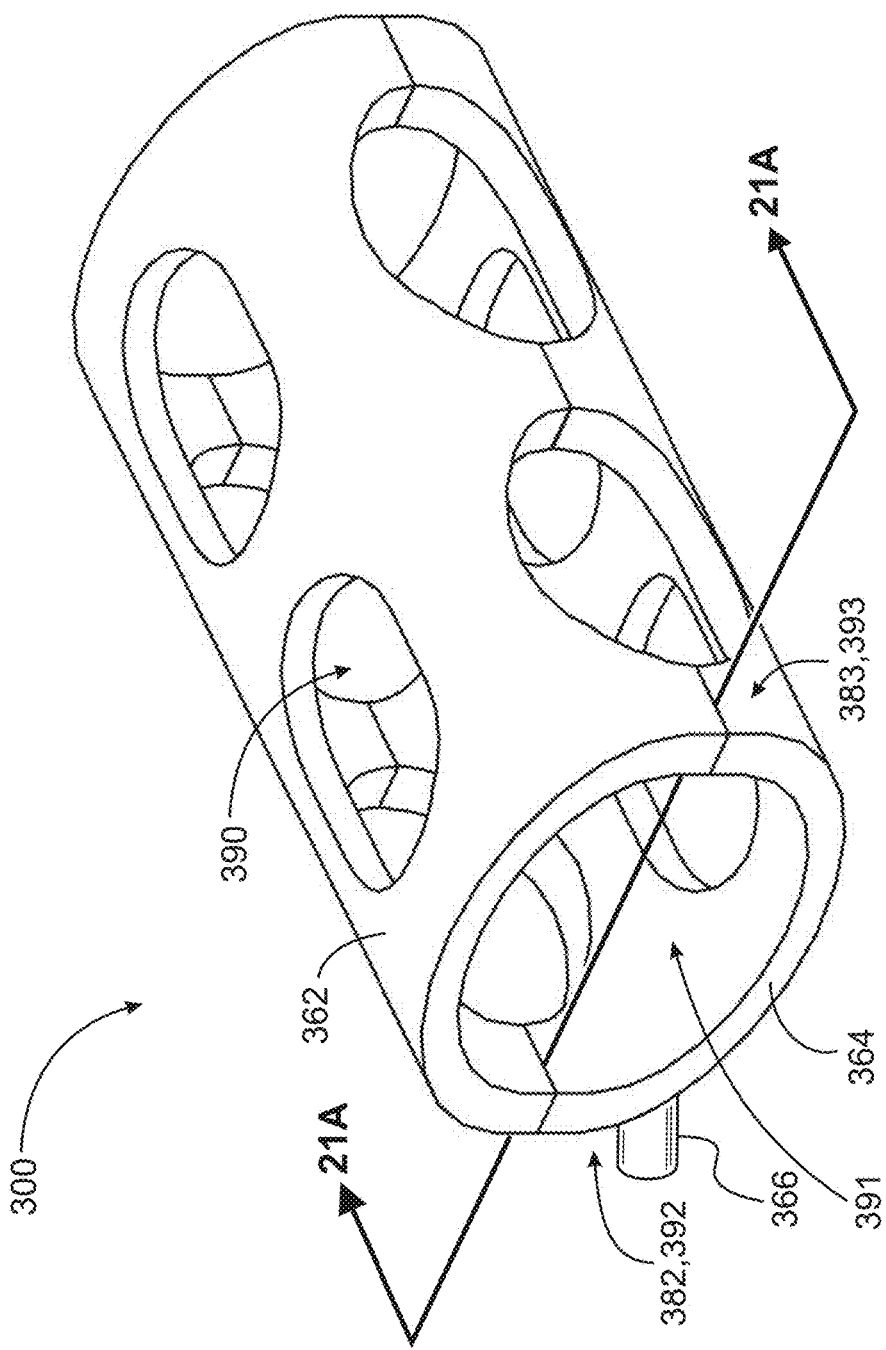
FIG. 19A is a perspective view of an expandable intervertebral fusion implant, in an unexpanded state having a first intermediate telescoping strut and a second intermediate telescoping strut.
Figure 19B:
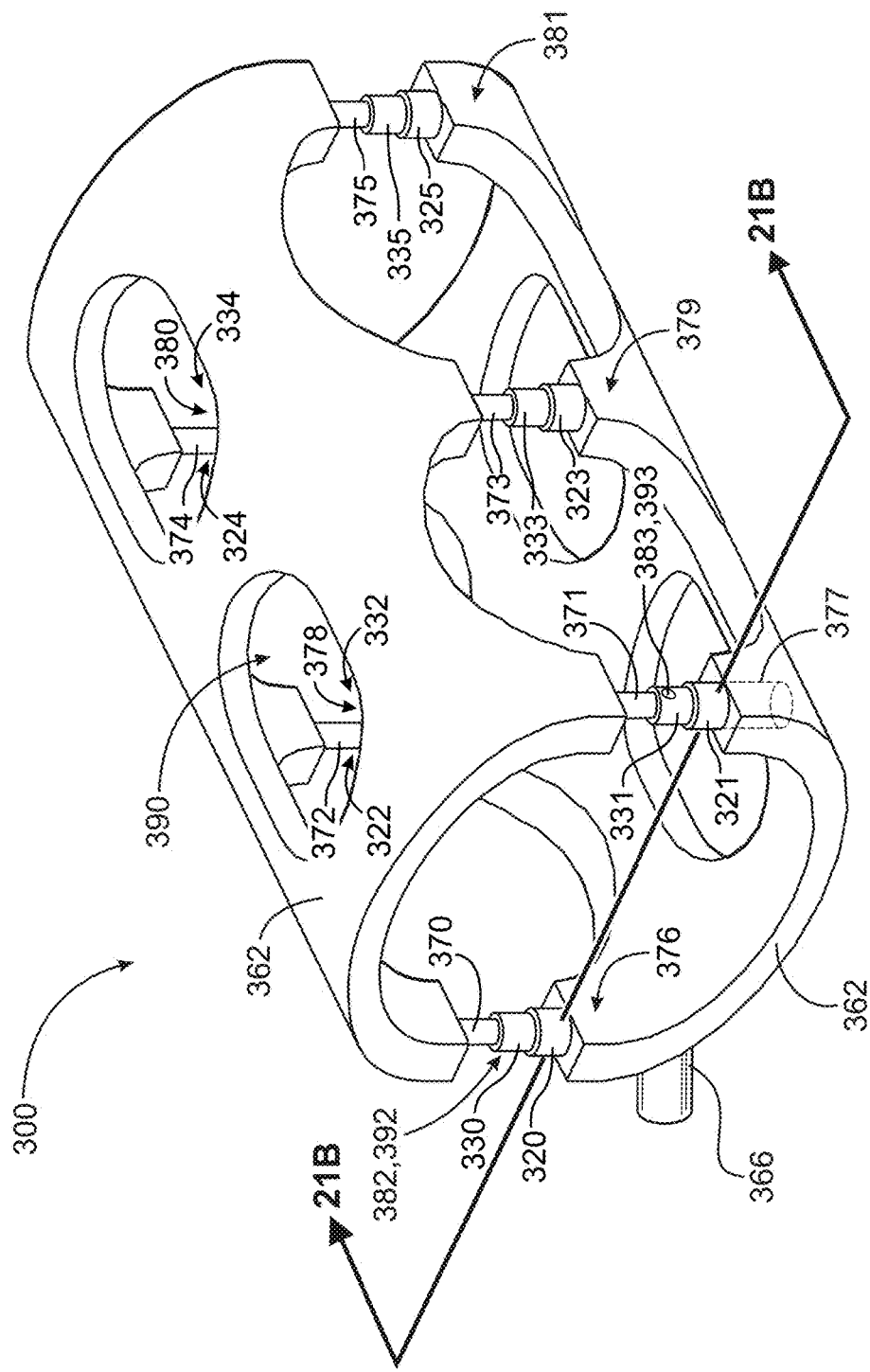
FIG. 19B is a perspective view of an expandable intervertebral fusion implant, in an expanded state having a first intermediate telescoping strut and a second intermediate telescoping strut.

FIGS. 19A and 19B are perspective views of expandable intervertebral fusion implant 300, in an unexpanded and an expanded state respectively. Expandable intervertebral fusion implant 300 comprises a plurality of first intermediate telescoping struts 320, 321, 322, 324, 324 and 325, and a plurality of second intermediate telescoping struts 330 331, 332, 333, 334, and 335. Expandable intervertebral fusion implant 300 further comprises superior component 362, inferior component 364, and input port 366. Superior and inferior components 362 and 364 are telescopingly engagable. Superior component 362 comprises a body with a generally arcuate shape (quasi-elliptical cross-section), although implants of other shapes are certainly possible and intended to be within the scope of the appended claims. The body is shown as having at least one aperture 190. Inferior component 364 also comprises a body with an arcuate shape, having at least one aperture 390 and input port 366. The inferior and superior components are of similar shapes and dimensions so as to be capable of matingly engaging one another. When expandable intervertebral fusion implant 300 is in the unexpanded state, superior component 362 and inferior component 364 form a hollow, substantially tubular structure having a cavity 388.

Superior component 362 further comprises a plurality of downwardly extending struts 370, 371, 372, 373, 374 and 375. Inferior component 364 further comprises a plurality of upwardly extending hollow channels 376, 377, 378, 379, 380 and 381; a plurality of first intermediate telescoping struts 320, 321, 322, 323, 324 and 325; and, a plurality of second intermediate telescoping struts 330, 331, 332, 333, 334 and 335. The plurality of upwardly extending hollow channels 376, 377, 378, 379, 380 and 381 receive, and telescopingly engage, the plurality of first intermediate telescoping struts 320, 321, 322, 323, 324 and 325 respectively. The plurality of first intermediate telescoping struts 320, 321, 322, 323, 324 and 325 receive, and telescopingly engage, the plurality of second intermediate telescoping struts 330, 331, 332, 333, 334 and 335 respectively. The plurality of second intermediate telescoping struts 330, 331, 332, 333, 334 and 335 receive, and telescopingly engages, downwardly extending struts 370, 371, 372, 373, 374 and 375, respectively. The plurality of upwardly extending hollow channels 376, 377, 378, 379, 380 and 381 are also connected to input port 366.

It should be appreciated that the present embodiment as claimed is not limited to struts comprising only two telescoping members. For example, the expandable intervertebral fusion implant may comprise a third intermediate telescoping member arranged to telescopingly engage the second intermediate telescoping member, although this is not shown in the drawings. The embodiment could have even more than three telescoping members.

Figure 20A:
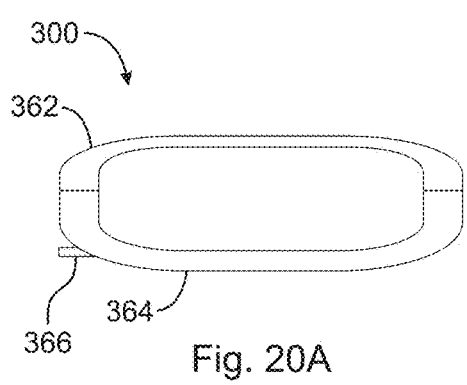
FIG. 20A is a front view of an expandable intervertebral fusion implant, in an unexpanded state having a first intermediate telescoping strut and a second intermediate telescoping strut.
Figure 20B:
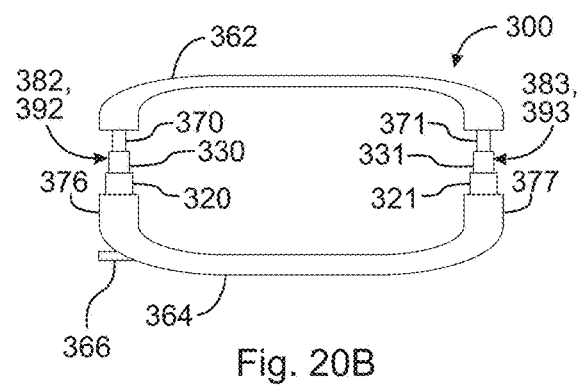
FIG. 20B is a front view of an expandable intervertebral fusion implant, in an expanded state having a first intermediate telescoping strut and a second intermediate telescoping strut.
Figure 21A:
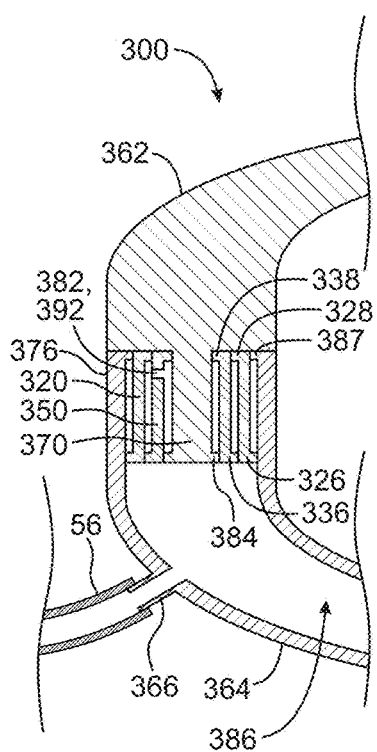
FIG. 21A is a partial cross-sectional view of an expandable intervertebral fusion implant in FIG. 20A, in an unexpanded state taken generally along line 21A-21A in FIG. 19A.

FIG. 20A is a front view of an expandable intervertebral fusion implant, in an unexpanded state having a first intermediate telescoping strut and a second intermediate telescoping strut FIG. 20B is a front view of an expandable intervertebral fusion implant, in an expanded state having a first intermediate telescoping strut and a second intermediate telescoping strut FIG. 21A a partial cross-sectional view of expandable intervertebral fusion implant 300 in FIG. 20B, in an unexpanded state taken generally along line 21A-21A in FIG. 19A having a plurality of first intermediate telescoping struts 320, 321, 322, 323, 324 and 325 and a plurality of second intermediate telescoping struts 330, 331, 332, 333, 334 and 335. Inferior component 364 further comprises channel 386 that connects the plurality of upwardly extending hollow channels 376, 377, 378, 379, 380 and 381. Upwardly extending hollow channels 376, 377, 378, 379, 380 and 381 further comprise a plurality of first intermediate telescoping struts 320, 321, 322, 323, 324 and 325 and a plurality of second intermediate telescoping struts 330, 331, 332, 333, 334 and 335, as well as, retention shoulder 387. Each of the plurality of first intermediate telescoping struts 320, 321, 322, 323, 324 and 325 further comprise a first intermediate flange, and a first intermediate retention shoulder. (Only one of the six first intermediate retention shoulders, 228, and one of the six intermediate flanges, 326, are shown in the drawings.) Each of the plurality of second intermediate telescoping struts 330, 331, 332, 333, 334 and 335 further comprise a second intermediate flange, a second intermediate retention shoulder, and a vent. (Only one of the six intermediate retention shoulders, 328, one of the six intermediate flanges, 326, and one of the six vents 382 are shown in the drawings.)

Figure 21B:
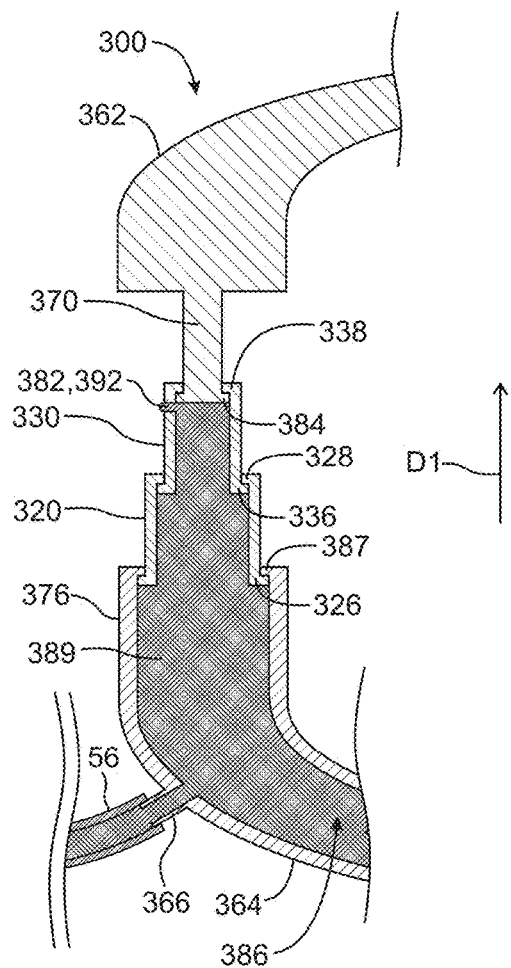
FIG. 21B is a partial cross-sectional view of an expandable intervertebral fusion implant in FIG. 20B, in an expanded state taken generally along line 21B-21B in FIG. 19B.

FIG. 21B is a partial cross-sectional view of expandable intervertebral fusion implant 300 in FIG. 20B, in an expanded state taken generally along line 21B-21B in FIG. 19B. Hardenable material 389 is injected via input port 366, filling the plurality of upwardly extending hollow channels 376, 377, 378, 379, 380 and 381, as well as channel 386. Injecting hardenable material 389 creates hydraulic pressure within the hollow channels and forces the plurality of downwardly extending struts 370, 371, 372, 373, 374 and 375; the plurality of first intermediate telescoping struts 320, 321, 322, 323, 324 and 325; and, the plurality of second intermediate telescoping struts 330, 331, 332, 333, 334 and 335 in a first direction D1, displacing superior component 362 in a first direction D1.

Each of the downwardly extending struts 370, 371, 372, 373, 374 and 375 further comprises a flange operatively arranged to limit movement of each of the second plurality of intermediate struts within its respective channel. As hardenable material 389 is introduced via port 366, and evenly distributed to upwardly extending hollow channels 376, 377, 378, 379, 380 and 381, the plurality of first intermediate telescoping struts 320, 321, 322, 323, 324 and 325; and, the plurality of second intermediate telescoping struts 330, 331, 332, 333, 334 and 335 through channel 386, the downwardly extending struts 370, 371, 372, 373, 374 and 375, the plurality of first intermediate telescoping struts 320, 321, 322, 323, 324 and 325, and the plurality of second intermediate telescoping struts 330, 331, 332, 333, 334 and 335, are displaced in a first direction D1, displacing superior component 362, in a first direction D1. Upwardly extending hollow channels 376, 377, 378, 379, 380 and 381, the plurality of first intermediate telescoping struts 320, 321, 322, 323, 324 and 325, and the plurality of second intermediate telescoping struts 330, 331, 332, 333, 334 and 335, as well as, channel 386 continue to fill with hardenable material 389 until each flange of each of the downwardly extending struts 370, 371, 372, 373, 374 and 375 contact each respective second intermediate shoulder of each of the second plurality of intermediate telescoping struts 330, 331, 332, 333, 334 and 335; and each respective second intermediate flange contacts each respective first intermediate retention shoulder; and, each respective first intermediate flange contacts each respective shoulder of each of the upwardly extending hollow channels 376, 377, 378, 379, 380 and 381, stopping the displacement of superior component 362 in a first direction D1.

As hardenable material 389 is injected into upwardly extending hollow channels 376, 377, 378, 379, 380 and 381, the air originally contained within the hollow channels, the plurality of first intermediate telescoping struts, the plurality of second intermediate telescoping struts, and channel 386, escapes via vents. Each of the plurality of second intermediate struts 330, 331, 332, 333, 334 and 335 has a vent, although only one of the six vents are shown for illustration in the drawings. For example, second intermediate strut 330 has a vent 382 as shown in FIGS. 21A and 21B. When expandable intervertebral fusion implant 300 is in an expanded state, flange 384 is in contact with second intermediate retention shoulder 338, allowing hardenable material 389 to escape via vent 382. When hardenable material 389 escapes vent 382 instead of air, this signals that the upwardly extending hollow channels 376, 377, 378, 379, 380 and 381, the plurality of first intermediate telescoping struts 320, 321, 322, 323, 324 and 325, and the plurality of second intermediate telescoping struts 330, 331, 332, 333, 334 and 335, and channel 386 have completely filled with hardenable material 389. (The surgeon can actually see the hardenable material escaping through the vents with an endoscope.) When the surgeon sees the hardenable material escape through the vents, the surgeon is then free to cut injection tube 56 at input port 366, remove the injection tube, and let the hardenable material cure and harden, locking the implant in its expanded state. It should be understood that the vents within each respective second intermediate strut further contain a valve. For example, vent 382 further comprises valve 383 to allow control of the rate of escaping air and hydraulic pressure within the hollow channels, the first and second intermediate struts. Hardenable material 289 is preferably made of poly(methyl methacrylate), polycarbonate resins, epoxy resins, polyamide resins, or equivalent. Superior component 362 and inferior component 364 of expandable intervertebral fusion implant 300 are preferably made of polyether ether ketone and titanium, or equivalent.

FIG. 22A is a side view of a hingedly expandable intervertebral fusion implant 400, in an unexpanded state. Hingedly expandable intervertebral fusion implant 400 broadly comprises a superior component 462, an inferior component 464, a hinge 408, an input port 466, and a vent 482.

FIGS. 22B and 22C are front views of hingedly expandable intervertebral fusion implant 400, in an unexpanded and expanded state respectively.

FIG. 22D is a cross-sectional view of hingedly expandable intervertebral fusion implant 400 as shown in FIG. 22A, in an unexpanded state taken generally along line 22D-22D in FIG. 22B. Superior component 462 further comprises downwardly extending strut 470. Downwardly extending strut 470 further comprises a flange 484. Inferior component 464 further comprises an upwardly extending hollow channel 476. Upwardly extending hollow channel further comprises a shoulder 487. Input port 466 is operatively arranged to deliver a hardenable material 489 into upwardly extending hollow channel 476. Vent 482 is operatively arranged to allow air to escape from the upwardly extending hollow channel 476 as hardenable material 489 is added to channel 476.

FIG. 22E is a cross-sectional view of hingedly expandable intervertebral fusion implant 400 in FIG. 22A, in an expanded state taken generally along line 22E-22E in FIG. 22C. As hardenable material 489 is injected, via input port 466, into upwardly extending hollow channel 476, hydraulic pressure is created within upwardly extending hollow channel 476, displacing downwardly extending strut 470 in a first direction D1. As downwardly extending strut 470 is displaced in first direction D1, superior component 462 is rotationally displaced about axis of rotation AR. Hardenable material 489 is injected until flange 484 of downwardly extending strut 470 abuts shoulder 487 of upwardly extending hollow channel 476. When hardenable material 489 escapes vent 482 instead of air, this signals that channel 476 has completely filled with hardenable material. (The surgeon can actually see the hardenable material escaping through the vents with an endoscope.) When the surgeon sees the hardenable material escape through the vents, the surgeon is then free to cut injection tube 56 at input port 466, remove the injection tube, and let the hardenable material cure and harden, locking the implant in its expanded state. Vent 482 further comprises valve 492 to allow control of the rate of escaping air and hydraulic pressure within the hollow channel. Hardenable material 489 is preferably made of poly(methyl methacrylate), polycarbonate resins, epoxy resins, polyamide resins, or equivalent. Superior component 462 and inferior component 464 of expandable intervertebral fusion implant 400 are preferably made of polyether ether ketone and titanium, or equivalent.

FIG. 22F is a perspective view of hingedly expandable intervertebral fusion implant 400, in an expanded state. Superior component 462 and inferior component 464 are shown as having at least one aperture 490 to accept bone fusing material.

FIG. 23A illustrates hingedly expandable intervertebral fusion implant 400 in place in disc space $D_{L3-L4}$, in an unexpanded state. As illustrated in FIG. 23A, hingedly expandable intervertebral fusion implant 400 can be placed within disc space $D_{L3-L4}$ where vertebrae L3 and vertebrae L4 as misaligned.

FIG. 23B illustrates hingedly expandable intervertebral fusion implant 400 in place in disc space $D_{L3-L4}$, in an expanded state. As superior component 462 is rotationally displaced about axis of rotation AR, vertebrae L3 is displaced in direction D1, correcting misalignment between vertebra L3 and L4. This alignment correcting procedure could be used to correct spinal misalignment in patients with scoliosis.

Figure 24:
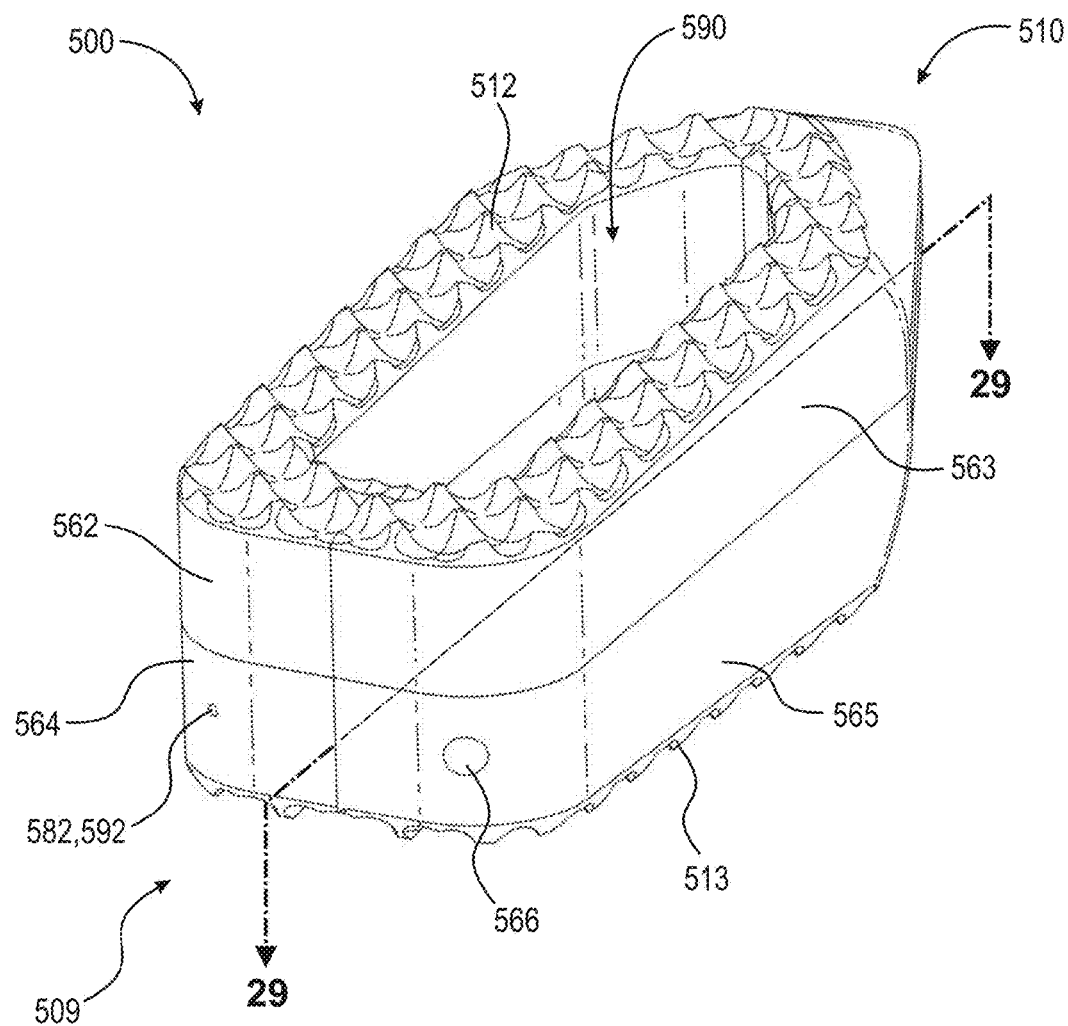
FIG. 24 is a perspective view of a bilaterally expandable intervertebral fusion implant, in an unexpanded state.

FIG. 24 is a perspective view of a bilaterally expandable intervertebral fusion implant 500, in an unexpanded state. Bilaterally expandable intervertebral fusion implant 500 comprises a first superior component 562, a second superior component 563, a first inferior component 564, and a second inferior component 565. First and second superior components 562 and 563 further comprise a toothed surface 512, and first and second inferior components 564 and 565 further comprise a toothed surface 513. Toothed surfaces 512 and 513 prevent bilaterally expandable intervertebral fusion implant 500 from shifting within a disc space. It should be appreciated that although toothed surfaces 512 and 513 are shown as having a toothed texture in FIGS. 24-28, any equivalent texture that will produce a sufficient static coefficient of friction between the superior components of the implant and the respective vertebra the implant is placed between, that prevents bilaterally expandable intervertebral fusion implant 500 from slipping laterally within the disc space could be utilized. Bilateral expandable intervertebral fusion implant 500 has a proximate end 509 and a distal end 510. First inferior component 564 comprises upwardly extending hollow channel 576 and vent 582. Second inferior component 565 further comprises upwardly extending hollow channel 577 and input port 566. First and second inferior components 564 and 565 contain upwardly extending hollow channels 576 and 577 respectively, to allow for the dispersion of a hardenable material 589 throughout the first and second inferior components. In its unexpanded state, the superior components and inferior components form an aperture 590, to receive bone fusing material.

Figure 25:
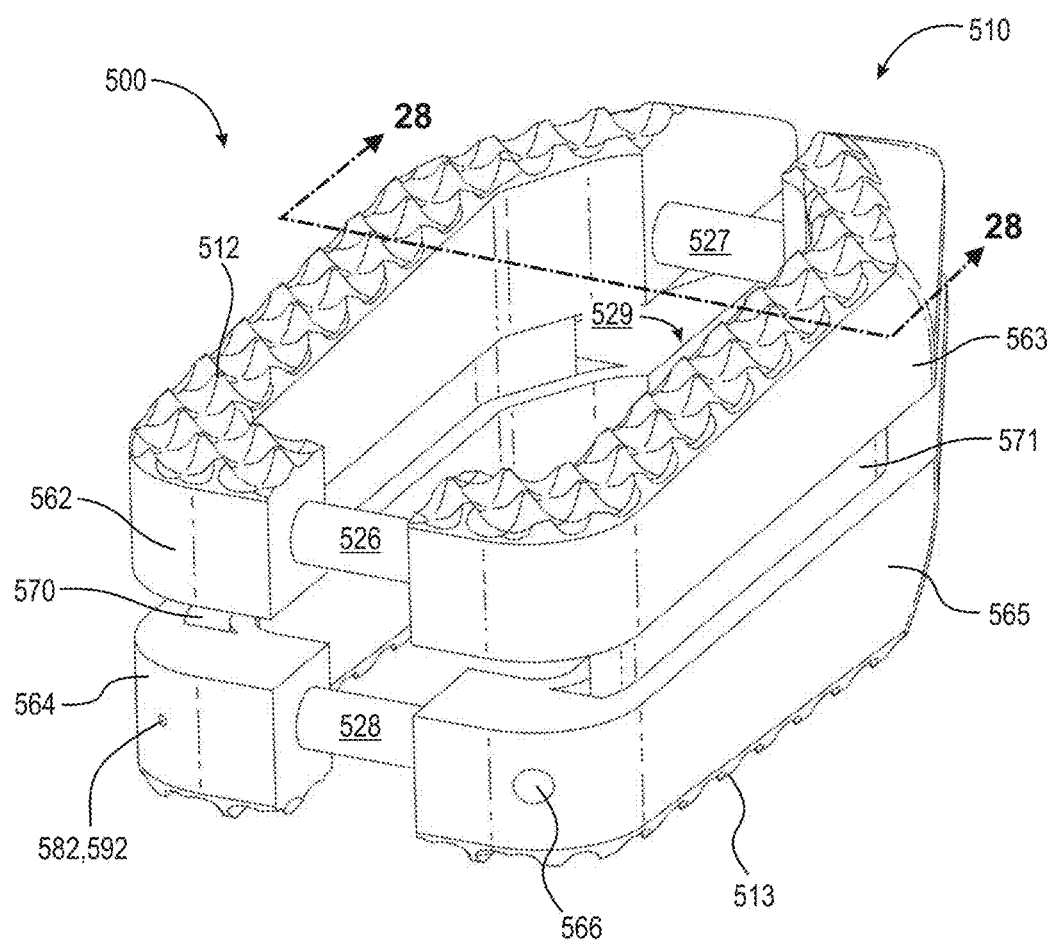
FIG. 25 is a perspective view of a bilaterally expandable intervertebral fusion implant, in an expanded state.
Figure 28:
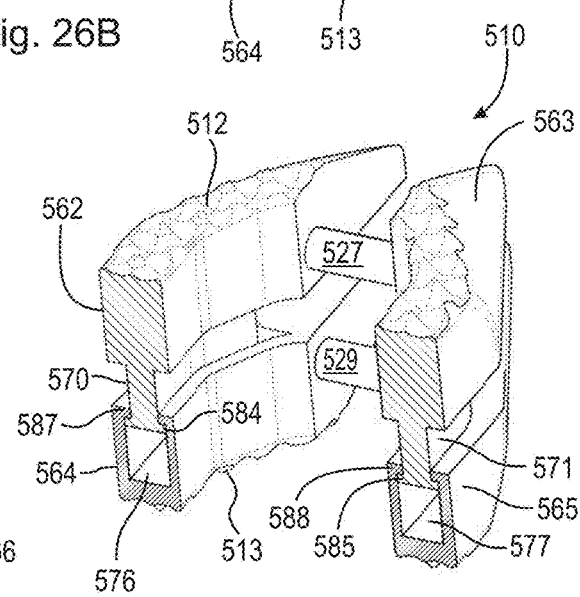
FIG. 28 is a cross-sectional view of a bilaterally expandable intervertebral fusion implant, in an expanded state taken generally along line 28-28 in FIG. 25.

FIG. 25 is a perspective view of bilaterally expandable intervertebral fusion implant 500, in an expanded state. First superior component 562 further comprises a downwardly extending strut wall 570. Second superior component 563 further comprises a downwardly extending strut wall 571. Upwardly extending hollow channel 576 is arranged to receive and telescopingly engage with downwardly extending strut wall 570. Upwardly extending hollow channel 577 is arranged to receive and telescopingly engage with downwardly extending strut wall 571. Each of upwardly extending hollow channels 576 and 577 further comprise a shoulder 587 and 588 respectively (as shown in FIG. 28).

First and second superior components 562 and 563 further comprise a first superior horizontal telescoping strut 526 and a second superior horizontal telescoping strut 527. As shown in FIG. 25, first superior horizontal telescoping strut 526 is arranged at the proximate end 509 of implant 500 and second superior horizontal telescoping strut 527 is arrange at the distal end 510 of implant 500. First and second inferior components 564 and 565 further comprise a first inferior horizontal telescoping strut 528 and a second inferior horizontal telescoping strut 529. First superior horizontal telescoping strut 528 is arranged at the proximate end 509 of implant 500 and second superior horizontal telescoping strut 529 is arrange at the distal end 510 of implant 500.

Figure 26A:
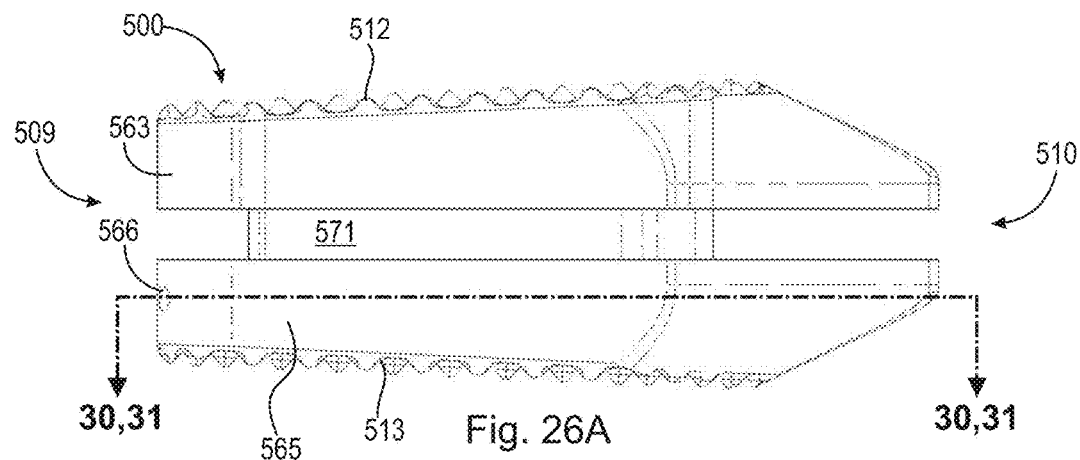
FIG. 26A is a side view of a bilaterally expandable intervertebral fusion implant, in an expanded state.

FIG. 26A is a side view of bilaterally expandable intervertebral fusion implant 500, in an expanded state.

Figure 26B:
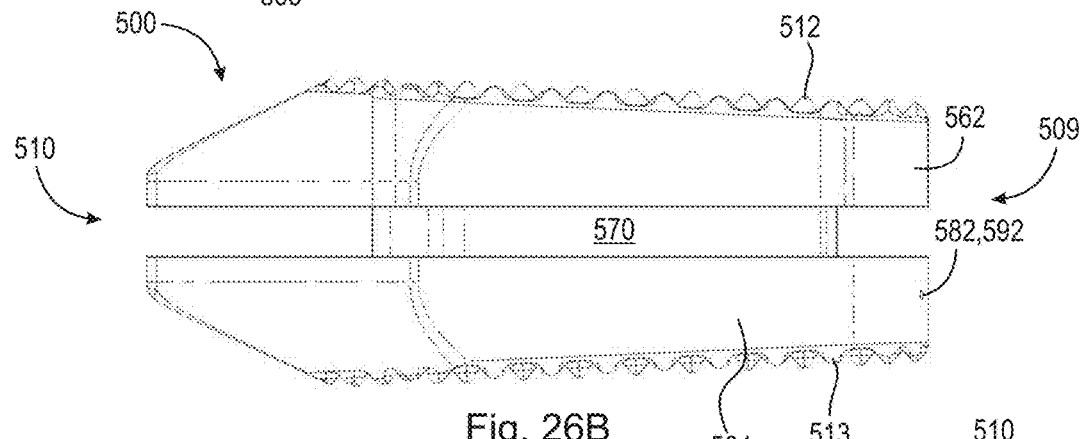
FIG. 26B is an opposite side view of a bilaterally expandable intervertebral fusion implant, in an expanded state.

FIG. 26B is an opposite side view of a bilaterally expandable intervertebral fusion implant 500, in an expanded state.

Figure 27:
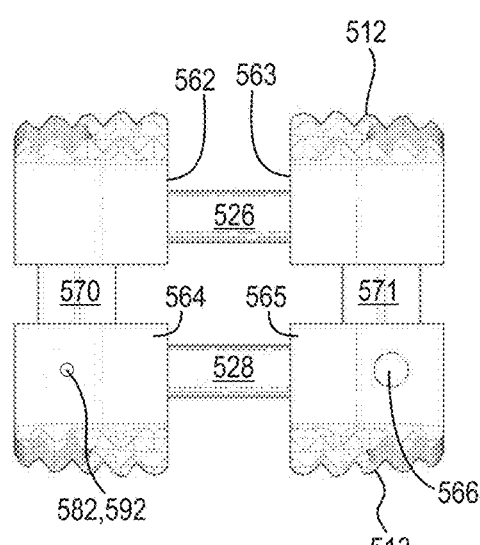
FIG. 27 is a front view of a bilaterally expandable intervertebral fusion implant, in an expanded state.

FIG. 27 is a front view of bilaterally expandable intervertebral fusion implant 500, in an expanded state.

FIG. 28 is a cross-sectional view of bilaterally expandable intervertebral fusion implant 500, in an expanded state taken generally along line 28-28 in FIG. 25. Upwardly extending hollow channels 576 and 577 as well as first and second inferior horizontal telescoping struts 527 and 528 are operatively arranged to receive and fill with hardenable material 589, injected via port 566. It should be appreciated that the present embodiment is positioned, vertically expanded, and horizontally expanded to the desirable dimensions manually, that is to say, not using hardenable material 589 to exert hydraulic pressure upon downwardly extending strut walls 570 and 571. However, it should also be appreciated that the present embodiment could be vertically and horizontally expanded using hydraulic pressure created by injecting hardenable material 589 into upwardly extending hollow channels 576 and 577.

Downwardly extending strut walls 570 and 571 each have a flange, 584 and 585 respectively, that are operatively arranged to limit movement of each downwardly extending strut wall within its respective upwardly extending hollow channel. For example, as shown in FIG. 28, Flange 584 of strut wall 570 is shown abutting shoulder 587 when the implant 500 is in a fully expanded state. As hardenable material is injected via port 566 into upwardly extending hollow channels 576 and 577 as well as first and second inferior horizontal telescoping struts 528 and 529, the surgeon could continue to hold the desired position of implant 500, or allow the implant to expand due to hydraulic pressure to its fully expanded state.

Figure 29:
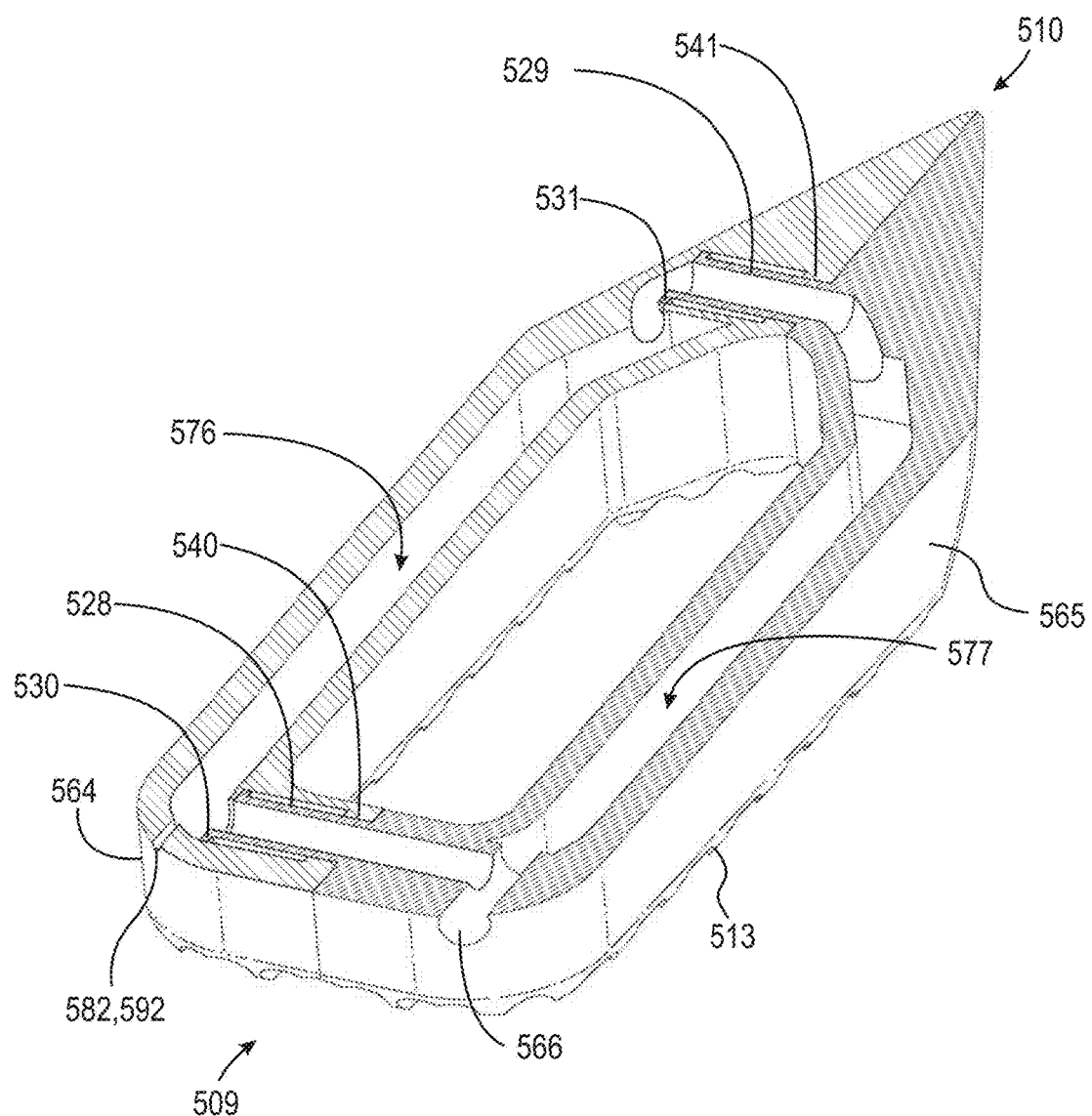
FIG. 29 is a cross-sectional view of a the inferior component of a bilaterally expandable intervertebral fusion implant, in an unexpanded state taken generally along line 29-29 in FIG. 24.

FIG. 29 is a cross-sectional view of bilaterally expandable intervertebral fusion implant 500, in an unexpanded state taken generally along line 29-29 in FIG. 24. First and second inferior horizontal telescoping struts 528 and 529 further comprise first inferior horizontal flange 530 and a second inferior horizontal flange 531 respectively. First inferior component 564 further comprises a first inferior horizontal shoulder 540 and a second inferior horizontal shoulder 541 respectively, and operatively arranged to limit the horizontal movement of first and second inferior horizontal telescoping struts 528 and 529 respectively. First and second superior horizontal telescoping struts 526 and 527 function similarly, although they are not shown in the drawings.

Figure 30:
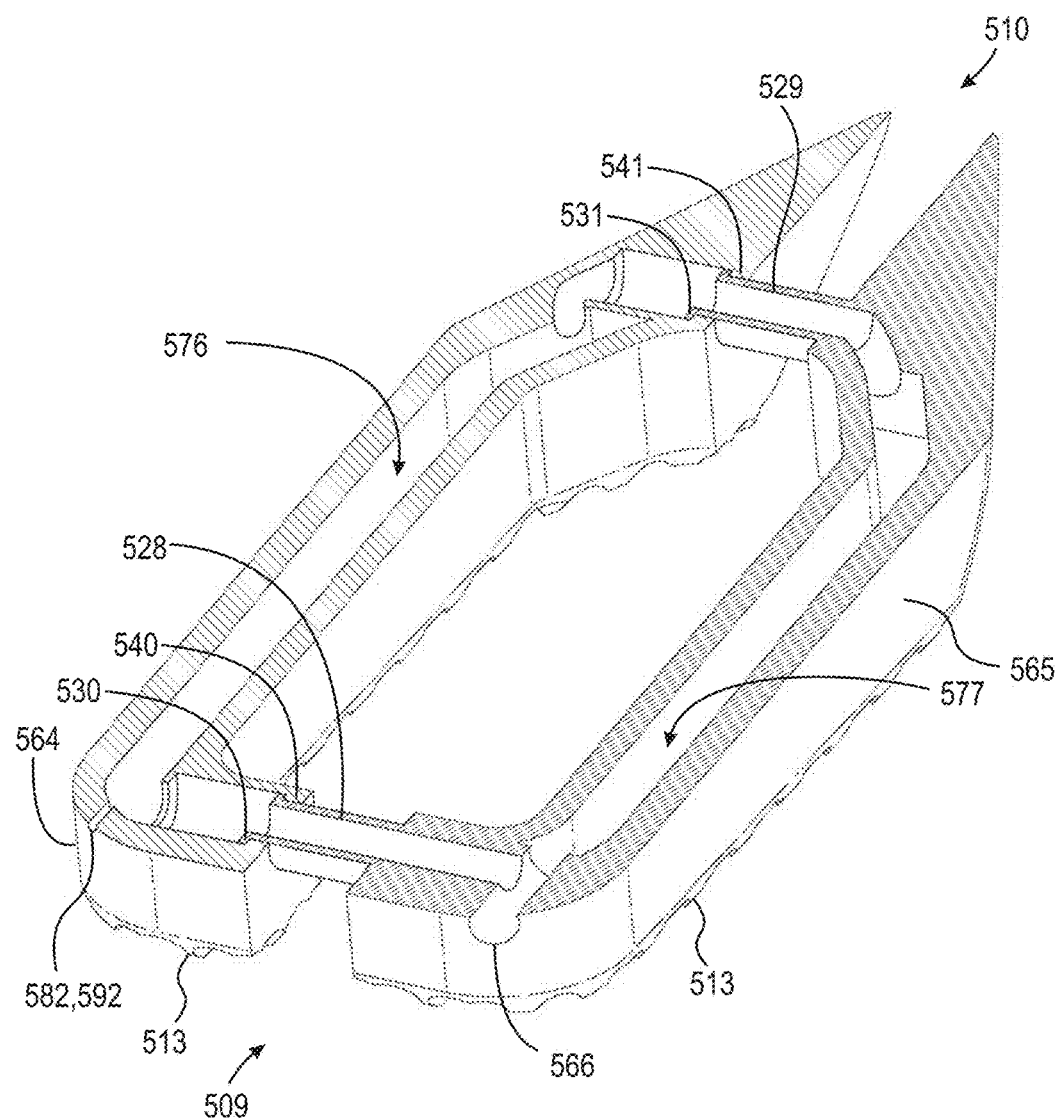
FIG. 30 is a cross-sectional view of a the inferior component of a bilaterally expandable intervertebral fusion implant, in an expanded state taken generally along line 30-30 in FIG. 26A; and, FIG. 31 is a cross-sectional view of a the inferior component of a bilaterally expandable intervertebral fusion implant, in an expanded state showing hardenable material taken along line 31-31 in FIG. 26A.
Figure 31:
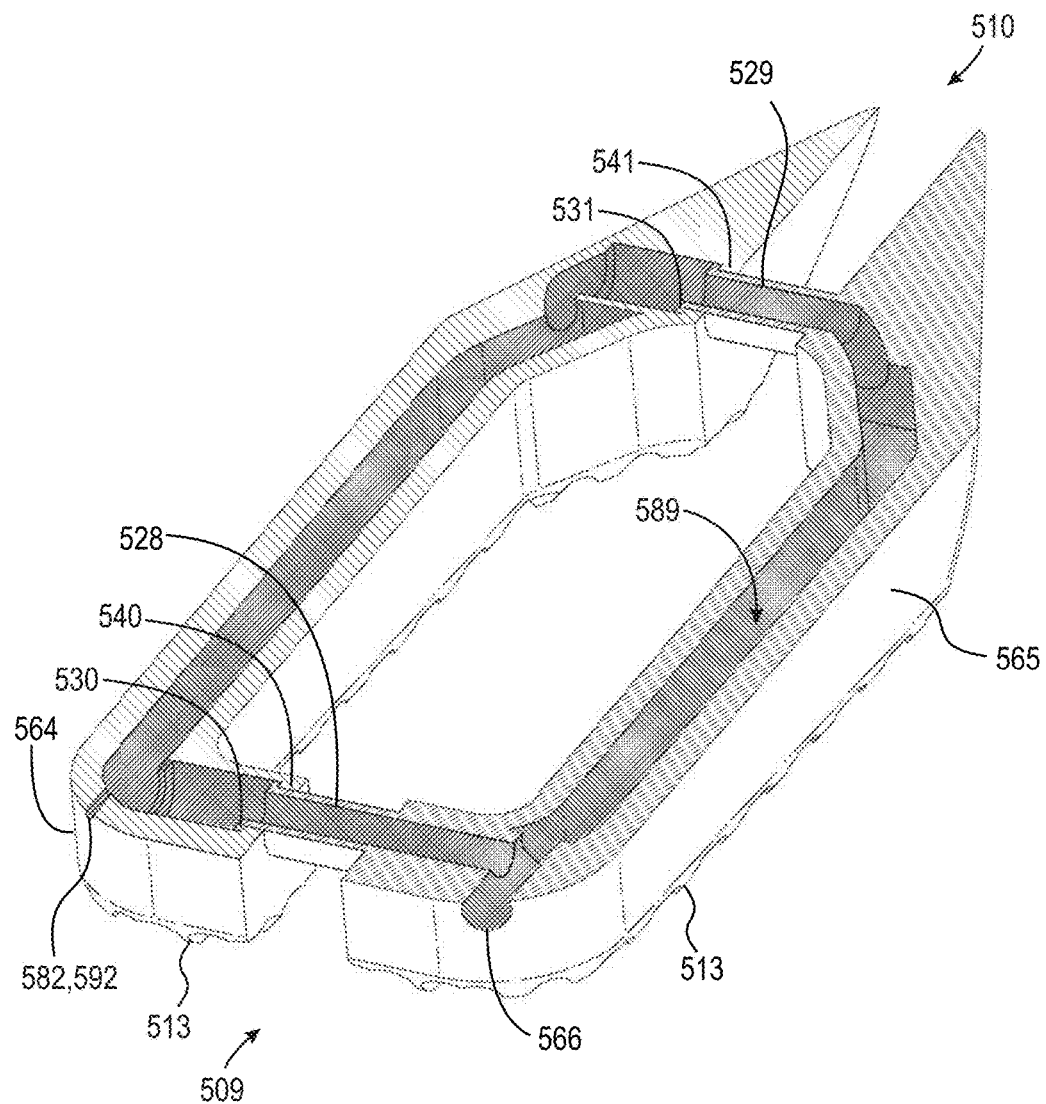

FIG. 30 is a cross-sectional view of bilaterally expandable intervertebral fusion implant 500, in an expanded state taken generally along line 30-30 in FIG. 26A; and, FIG. 31 is a cross-sectional view of bilaterally expandable intervertebral fusion implant 500, in an expanded state taken along line 31-31 in FIG. 26A. This figure illustrates hardenable material 589 filling upwardly extending hollow channels 576 and 577 as well as first and second inferior horizontal struts 528 and 529. When hardenable material 589 escapes vent 582 instead of air, this signals that channels 576 and 577 and horizontal struts 528 and 529 are completely filled with hardenable material. (The surgeon can actually see the hardenable material escaping through the vent with an endoscope.) When the surgeon sees the hardenable material escape through the vent, the surgeon is then free to cut injection tube 56 at input port 566, remove the injection tube, and let the hardenable material cure and harden, locking the implant in its expanded state. Vent 582 further comprises valve 592 to allow control of the rate of escaping air and hydraulic pressure within the hollow channel. Hardenable material 589 is preferably made of poly (methyl methacrylate), polycarbonate resins, epoxy resins, polyamide resins, or equivalent. Superior components 562 and 563, as well as, and inferior components 564 and 565 of expandable intervertebral fusion implant 500 are preferably made of polyether ether ketone and titanium, or equivalent.

It should be appreciated that hardenable materials 89, 189, 289, 389, 489 and 589 are intended to be injected into ports 66, 166, 266, 366, 466, and 566 using a hydraulic pump or other suitable means for injecting material through injection tube 56. It should be further understood that the expandable intervertebral implants described herein are applicable to all generally accepted surgical approaches, including microsurgical and endoscopic applications.

Thus it is seen that the objects of the invention are efficiently obtained, although changes and modifications to the invention should be readily apparent to those having ordinary skill in the art, which changes would not depart from the spirit and scope of the invention as claimed.

LIST OF REFERENCE NUMBERS

10 Spinal column
C1-C7 Cervical vertebrae
T1-T9 Thoracic vertebrae
L1-L5 Lumbar vertebrae
S Sacrum
C Coccyx
D1 Direction
D2 Direction
D3 Direction
$D_{L1-L2}$ Disc
$D_{L2-L3}$ Disc
$D_{L3-L4}$ Disc
$D_{L4-L5}$ Disc
F Facet
FJ Facet joint
$h_1$ Collapsed height
$h_2$ Expanded height
SP Spinous process
TP Transverse process
IF Intervertebral foramen
A Annulus
AR Axis of rotation
N Nucleus
50 Distractor
52 Means of attachment
54 Disk Space
56 Injection tube
58 Upper spacer
59 Lower spacer
60 Expandable intervertebral fusion implant
62 Superior component
64 Inferior component
66 Input port
70 Downwardly extending strut
71 Downwardly extending strut
72 Downwardly extending strut
73 Downwardly extending strut
74 Downwardly extending strut
75 Downwardly extending strut
76 Upwardly extending hollow channel
77 Upwardly extending hollow channel
78 Upwardly extending hollow channel 79 Upwardly extending hollow channel
80 Upwardly extending hollow channel
81 Upwardly extending hollow channel
82 Vent
83 Vent
84 Flange
85 Flange
86 Channel
87 Shoulder
88 Shoulder
89 Hardenable material
90 Aperture
91 Cavity
92 Valve
93 Valve
100 Expandable intervertebral fusion implant
162 Superior component
164 Inferior component
166 Input port
170 Upwardly extending strut
171 Upwardly extending strut
172 Upwardly extending strut
173 Upwardly extending strut
174 Upwardly extending strut
175 Upwardly extending strut
176 Downwardly extending hollow channel
177 Downwardly extending hollow channel
178 Downwardly extending hollow channel
179 Downwardly extending hollow channel
180 Downwardly extending hollow channel
181 Downwardly extending hollow channel
182 Vent
183 Vent
184 Flange
185 Flange
186 Channel
187 Shoulder
188 Shoulder
189 Hardenable material
190 Aperture
191 Cavity
192 Valve
193 Valve
200 Expandable intervertebral fusion implant
220 Intermediate telescoping strut
221 Intermediate telescoping strut
222 Intermediate telescoping strut
223 Intermediate telescoping strut
224 Intermediate telescoping strut
225 Intermediate telescoping strut
226 Intermediate flange
227 Intermediate flange
228 Intermediate retention shoulder
229 Intermediate retention shoulder
262 Superior component
264 Inferior component
266 Input port
270 Downwardly extending strut
271 Downwardly extending strut
272 Downwardly extending strut
273 Downwardly extending strut
274 Downwardly extending strut
275 Downwardly extending strut
276 Upward extending hollow channel
277 Upward extending hollow channel
278 Upward extending hollow channel
279 Upward extending hollow channel
280 Upward extending hollow channel
281 Upward extending hollow channel
282 Vent
283 Vent
284 Flange
285 Flange
286 Channel
287 Shoulder
288 Shoulder
289 Hardenable material
290 Aperture
291 Cavity
292 Valve
293 Valve
300 Expandable intervertebral fusion implant
320 First intermediate telescoping strut
321 First intermediate telescoping strut
322 First intermediate telescoping strut
323 First intermediate telescoping strut
324 First intermediate telescoping strut
325 First intermediate telescoping strut
326 First intermediate flange
327 First intermediate flange
328 First intermediate retention shoulder
329 First intermediate retention shoulder
330 Second intermediate telescoping strut
331 Second intermediate telescoping strut
332 Second intermediate telescoping strut
333 Second intermediate telescoping strut
334 Second intermediate telescoping strut
335 Second intermediate telescoping strut
336 Second intermediate flange
337 Second intermediate flange
338 Second intermediate retention shoulder
339 Second intermediate retention shoulder
362 Superior component
364 Inferior component
366 Input port
370 Downwardly extending strut
371 Downwardly extending strut
372 Downwardly extending strut
373 Downwardly extending strut
374 Downwardly extending strut
375 Downwardly extending strut
376 Upward extending hollow channel
377 Upward extending hollow channel
378 Upward extending hollow channel
379 Upward extending hollow channel
380 Upward extending hollow channel
381 Upward extending hollow channel
382 Vent
383 Vent
384 Flange
385 Flange
386 Channel
387 Shoulder
388 Shoulder
389 Hardenable material
390 Aperture
391 Cavity
392 Valve
393 Valve
400 Expandable intervertebral fusion implant
408 Hinge
462 Superior component
464 Inferior component
466 Input port 470 Downwardly extending strut
476 Upward extending hollow channel
482 Vent
484 Flange
487 Retention shoulder
490 Aperture
492 Valve
500 Expandable intervertebral fusion implant
509 Proximate end
510 Distal end
512 Superior toothed surface
513 Inferior toothed surface
526 First superior horizontal telescoping strut
527 Second superior horizontal telescoping strut
528 First inferior horizontal telescoping strut
529 Second inferior horizontal telescoping strut
562 First superior component
563 Second superior component
564 First inferior component
565 Second inferior component
566 Input port
570 Downwardly extending strut wall
571 Downwardly extending strut wall
576 Upwardly extending hollow channel
577 Upwardly extending hollow channel
582 Vent
584 Flange
585 Flange
586 Channel
587 Shoulder
588 Shoulder
589 Hardenable material
590 Aperture
592 Valve

I claim:

1. An expandable intervertebral fusion implant, comprising:
an inferior component;
a superior component telescopingly engageable with the inferior component; and,
an input port arranged in the inferior or the superior component;
wherein:
the inferior component or the superior component includes a vent; and,
when a first material is introduced through the input port and into the inferior or the superior component, the superior component is displaced in a first direction relative to the inferior component.

2. The expandable intervertebral fusion implant of claim 1, wherein the inferior component comprises a first upwardly extending hollow channel and the superior component comprises a first downwardly extending strut arranged to telescopingly engage the first upwardly extending hollow channel.

3. The expandable intervertebral fusion implant of claim 1, wherein the superior component comprises a first downwardly extending hollow channel and the inferior component comprises a first upwardly extending strut arranged to telescopingly engage the first upwardly extending hollow channel.

4. The expandable intervertebral fusion implant of claim 1, wherein the inferior and superior components are expandable in a second direction, different than the first direction.

5. The expandable intervertebral fusion implant of claim 4, wherein the inferior and superior components are expandable in a third direction, different than the first and second directions.

6. The expandable intervertebral fusion implant of claim 1, further comprising:
a first hollow channel;
a second hollow channel connected to the first hollow channel by a further hollow channel;
a first strut arranged to telescopingly engage the first hollow channel; and,
a second strut arranged to telescopingly engage the second hollow channel;
wherein the first, second, and further hollow channels are arranged to receive the first material.

7. The expandable intervertebral fusion implant of claim 1, further comprising a cavity formed between the inferior and superior components to receive bone fusing material.

8. The expandable intervertebral fusion implant recited in claim 1, wherein said inferior component comprises a body, and said body comprises at least one aperture therein.

9. The expandable intervertebral fusion implant recited in claim 1, wherein said superior component comprises a body, and said body comprises at least one aperture therein.

10. The expandable intervertebral fusion implant recited in claim 1, wherein said inferior component comprises a body, and said body is arcuate in shape.

11. The expandable intervertebral fusion implant recited in claim 1, wherein said superior component comprises a body, and said body is arcuate in shape.

12. The expandable intervertebral fusion implant recited in claim 1, further comprising:
a hollow channel including a shoulder, the hollow channel connected to the input port; and,
a strut arranged to telescopingly engage the hollow channel, the strut including a flange arranged to slide within the hollow channel, and abut the shoulder when the superior component is in a maximally extended position relative to the inferior component.

13. The expandable intervertebral fusion implant recited in claim 1, wherein the superior and inferior components are hingedly connected.

14. The expandable intervertebral fusion implant recited in claim 1, further comprising a first intermediate telescoping member arranged to telescopingly engage the inferior and superior components.

15. The expandable intervertebral fusion implant recited in claim 14, further comprising a second intermediate telescoping member arranged to telescopingly engage the first intermediate telescoping member.

16. The expandable intervertebral fusion implant of claim 1, wherein the vent comprises a valve.

17. An expandable intervertebral fusion implant having a proximal end and a distal end, the expandable intervertebral fusion implant comprising:
an inferior component;
a superior component arranged to telescopingly engage the inferior component; and,
an input port and a vent arranged within the inferior component or the superior component;
wherein when the superior component is expanded to a first position relative to the inferior component, a first material is introduced into and through the inferior component and/or the superior component to maintain the position of the superior and inferior components.

18. The expandable intervertebral fusion implant of claim 17, further comprising a hollow channel extending between the input port and the vent, the hollow channel within the inferior component.

19. The expandable intervertebral fusion implant of claim 17, further comprising a hollow channel extending between the input port and the vent, the hollow channel within the superior component.

20. The expandable intervertebral fusion implant of claim 17, wherein the vent comprises a valve.

* * * * *